(12) United States Patent
Donello et al.

(10) Patent No.: US 9,314,466 B2
(45) Date of Patent: Apr. 19, 2016

(54) METHODS FOR TREATING COGNITIVE DISORDERS USING 1-BENZYL-1-HYDROXY-2,3-DIAMINO-PROPYL AMINES, 3-BENZYL-3-HYDROXY-2-AMINO-PROPIONIC ACID AMIDES AND RELATED COMPOUNDS

(71) Applicant: Allergan, Inc., Irvine, CA (US)

(72) Inventors: John E. Donello, Dana Point, CA (US); Fabien J. Schwieghoffer, Val-de-mame (FR); Lauren M. Luhrs, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/184,343

(22) Filed: Feb. 19, 2014

(65) Prior Publication Data

US 2015/0231140 A1 Aug. 20, 2015
US 2016/0051555 A9 Feb. 25, 2016

Related U.S. Application Data

(63) Continuation of application No. 12/530,104, filed as application No. PCT/US2008/054938 on Feb. 26, 2008, now abandoned.

(60) Provisional application No. 60/893,207, filed on Mar. 6, 2007.

(51) Int. Cl.
| | |
|---|---|
| *C07D 295/192* | (2006.01) |
| *A61K 31/5375* | (2006.01) |
| *A61K 31/40* | (2006.01) |
| *A61K 31/4025* | (2006.01) |

(52) U.S. Cl.
CPC .............. *A61K 31/5375* (2013.01); *A61K 31/40* (2013.01); *A61K 31/4025* (2013.01); *C07D 295/192* (2013.01)

(58) Field of Classification Search
CPC .................................................. C07D 295/192
See application file for complete search history.

(56) References Cited

U.S. PATENT DOCUMENTS

| | | |
|---|---|---|
| 5,916,911 A | 6/1999 | Shayman et al. |
| 5,945,442 A | 8/1999 | Shayman et al. |
| 5,952,370 A | 9/1999 | Shayman et al. |
| 6,030,995 A | 2/2000 | Shayman et al. |
| 6,051,598 A | 4/2000 | Shayman et al. |
| 6,335,444 B1 | 1/2002 | Jinbo et al. |
| 2002/0115667 A1 | 8/2002 | Walkley et al. |
| 2002/0198240 A1 | 12/2002 | Shayman et al. |
| 2003/0153768 A1 | 8/2003 | Hirth |
| 2005/0101674 A1 | 5/2005 | Maurer et al. |
| 2010/0190792 A1 * | 7/2010 | Donello ............ A61K 31/5375 514/237.8 |

FOREIGN PATENT DOCUMENTS

| | | |
|---|---|---|
| EP | 782992 A1 | 9/1997 |
| JP | 62114946 | 5/1987 |
| WO | 0104108 A1 | 1/2001 |
| WO | 0138228 A1 | 5/2001 |
| WO | 0212185 A1 | 2/2002 |
| WO | 02062777 A2 | 8/2002 |
| WO | 03008399 A1 | 1/2003 |
| WO | 03045928 A1 | 6/2003 |
| WO | 2006081280 A1 | 8/2006 |
| WO | 2008011483 A2 | 1/2008 |
| WO | 2008011485 A2 | 1/2008 |
| WO | WO 2008/011487 * | 1/2008 |

OTHER PUBLICATIONS

Vunnam et al., Analogs of Ceramide that Inhibit Glucocerebroside Synthetase in Mouse Brain, Chem. Phys. Lipids, vol. 26, pp. 265-278, 1980.
Inokuchi et al., Preparation of the Active Isomer of 1-Phenyl-2-Decanoylamino-3-Morpholino-1-Propanol Inhibitor of Murine Glucocerebroside Synthetase, J. Lipid Res. 28, 565-571, 1987.
Radin et al., Use of an Inhibitor of Glucosylceramide Synthesis, D-1-Phenyl-2-Decanoylamino-3-Morpholino-1-Propanol, NeuroProtocols, 3(2), 145-55, 1993.
Abe et al., J. Lipid Res. 36, 611-621, 1995.
Mitchell et al,. Glycosyltransferase Inhibitors: SYnthese of D-threo-PDMP, L-threo-PDMP, and Other Brain Glucosylceramide Synthase Inhibitors from D- or L-Serine, Org. Chem., 63 (24), 8837-8842, 1998.
Miura et al, Synthesis and Evaluation of Morpholino- and Pyrrolidinosphingolipids as Inhibitors of Glucosylceramide Synthase, Bioorg. Med. Chem., 6, 1481-1498, 1998.
Shin et al., Stereoselective SYnthesis of Enantiomerically Pure D-threo-PDMP; Manipulations of a Core 2,3-Diamino Alchohol Unit, Tetrahedron asymmetry, 11, 3293-3301, 2000.
Nishida et al., Practical Synthesis of threo-(1S, 2S)- and Erythro-(1R, 2S)-1-Phenyl-2-Palmitoylamino-3-Morpholino-1-Propanol (PPMP) from L-Serine, Synlett, 4, 389-390, 1998.
Abe et al., Improved Inhibitors of Glucosylceramide Synthase, J. Biochem., 111, 191-196, 1992.
Lee et al., Improved Inhibitors of Glucosylceramide Synthase, J. Biol. Chem., 274, 21, 14662-14669, 1999.
Jimbo et al, Development of a New Inhibitor of Glucosylceramide Synthase, J. Biochem., 127(3), 485-91, 2000.
Husain et al., Syn-Selective Additions to Garner Aldehyde: Synthesis of a Potent Glucosylceramide Synthase Inhibitor, Tetrahedron Lett., 43, 8621-8623, 2002.
Slavish et al., New PDMP Analogues Inhibit Process Outgrowth in an Insect Cell Line, Bioorg. Med. Chem. Lett., 14, 1487-1490, 2004.
Kurosawa et al., C-Labelling of a Novel Atypical Beta-Adrenoceptor Agonist, SM-11044, Journal of Labelled Compounds & Radiopharmaceuticals (1996), 38(3), 285-97.
Kastron et al. Latvijas PSR Zinatnu Akademijas Vestis, Kimijas Serija (1965) (4), 474-7.
Patent Cooperation Treaty, International Search Report, Jun. 2, 2008, PCT Application No. PCT/US2008/054938.
Forchetti CM, Treating Patients with Moderate to Severe Alzheimer's Disease: Implications of Recent Pharmacologic Studies, Prim. Care Companion J Clin Psychiatry, 2005; 7(4).
Yamagishi et al., A Synthetic Ceramide Analog Ameliorates Spatial Cognition Deficit and Stimulates Biosynthesis of Brain Gangliosides in Rats with Cerebral Ischemia, European Journal of Pharmacology, Feb. 21, 2003, vol. 462, No. 1-3, pp. 53-60.
Schneider et al., The Synthetic Analog 1-PDMP Partially Protects Striatal Dopamine Levels But Does Not Promote Dopamine Neuron Survival in Murine Models of Parkinsonism, Brain Research, Jul. 12, 2006, vol. 1099, No. 1, pp. 199-205.
Merck Research Laboratories, The Merck Manual of Diagnosis and Therapy, 2006, pp. 1781-1789 and 1808-1822.

* cited by examiner

*Primary Examiner* — Rebecca Anderson
(74) *Attorney, Agent, or Firm* — Jonathan Bass

(57) ABSTRACT

Disclosed herein are methods of treating a patient suffering from a cognitive disorder using the following compounds:

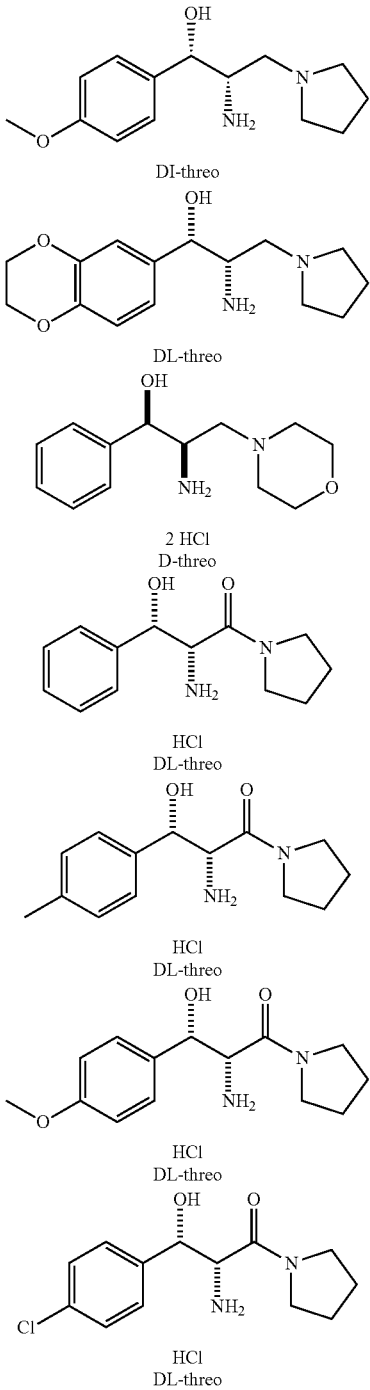
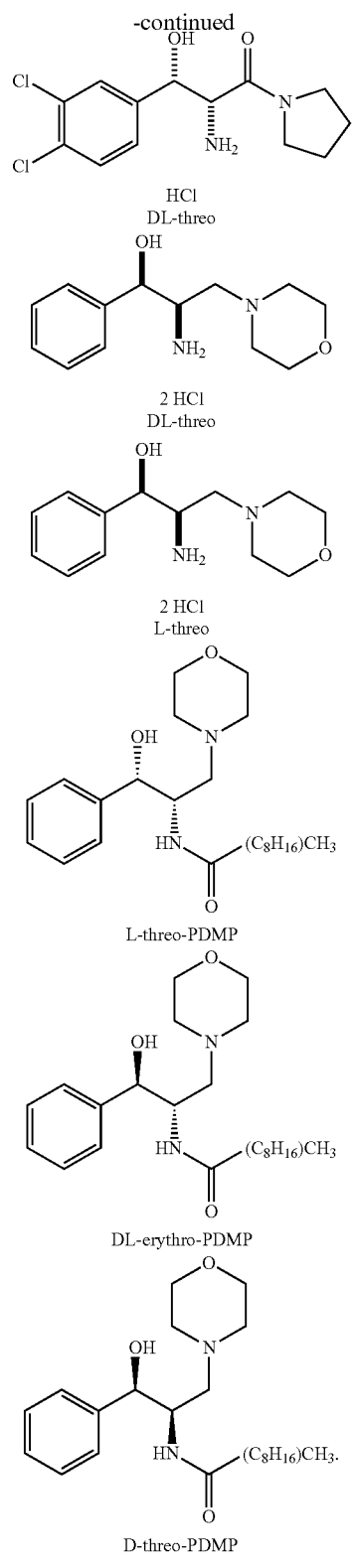

1 Claim, No Drawings

US 9,314,466 B2

METHODS FOR TREATING COGNITIVE DISORDERS USING 1-BENZYL-1-HYDROXY-2,3-DIAMINO-PROPYL AMINES, 3-BENZYL-3-HYDROXY-2-AMINO-PROPIONIC ACID AMIDES AND RELATED COMPOUNDS

CROSS REFERENCE TO RELATED APPLICATIONS

This application is a continuation of U.S. application Ser. No. 12/530,104, filed Mar. 22, 2010, which is a national stage application under 35 U.S.C. §371 of PCT application PCT/US2008/054938, filed on Feb. 26, 2008, which claims the benefit of U.S. provisional application Ser. No. 60/893,207, filed on Mar. 6, 2007, all of which are incorporated herein by reference in their entirety.

BACKGROUND OF THE INVENTION

1. Field of the Invention

The present invention is directed to methods of treating a patient suffering from one or more types of cognitive disorders using 1-benzyl-1-hydroxy-2,3-diamino-propyl amines, 3-benzyl-3-hydroxy-2-amino-propionic acid amides and related compounds.

2. Background of the Invention

1-Phenyl-2-decanoylamino-3-morpholino-1-propanol (PDMP) was discovered by Vunam, R. R. and Radin, N., Chem. Phys. Lipids, 26, 265-278, 1980. Preparation of PDMP is described in Inokuchi, J. et al., J. Lipid Res. 28, 565-571, 1987; Radin, A. et al., NeuroProtocols, 3(2), 145-55, 1993; Abe et al., J. Lipid Res. 36, 611-621, 1995 and U.S. Pat. No. 5,916,911.

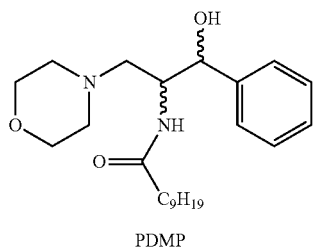

PDMP mixture of DL-erythro and DL-threo isomers

The isomers most active have the R,R-(D-threo)-configuration.

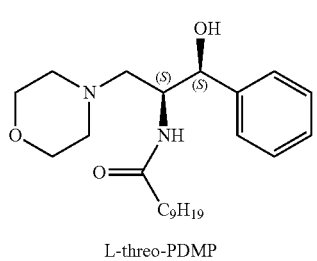

L-threo-PDMP

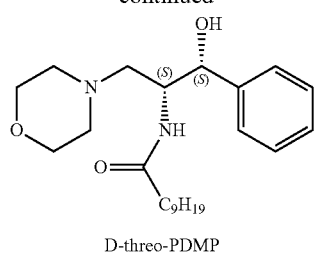

D-threo-PDMP

Preparation of enantiomerically pure D-threo-PDMP has been reported by Mitchell, Scott A. [J. Org. Chem., 63 (24), 8837-8842, 1998]; Miura, T. et al, [Bioorg. Med. Chem., 6, 1481-1498, 1998]; Shin, S. et al., [Tetrahedron asymmetry, 11, 3293-3301, 2000]; WO 2002012185

A stereoselective synthesis of enantiomerically pure D-threo-PDMP has also been described by Shin, S. et al., Tetrahedron asymmetry, 11, 3293-3301, 2000 and WO 2002012185 the key step is the regioselective cleavage by nitrogen nucleophiles, as morpholine, of the C(3)-N-bond of non-activated enantiomerically pure aziridine-2-methanols.

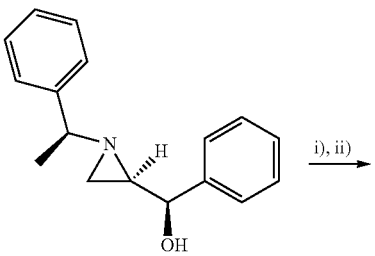

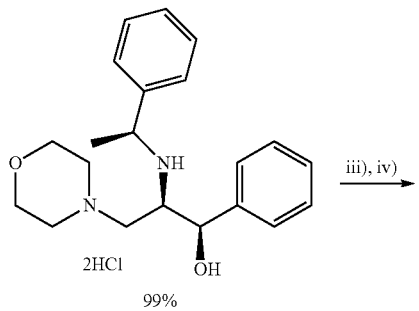

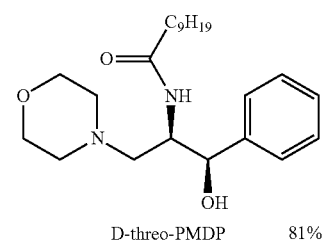

D-threo-PMDP    81% i) TMS-I, CH$_2$CN ii) a) morpholine b) HCl iii) Pd(OH)$_2$, H$_2$, AcOH, MeOH, 40° C.
iv)10% NaOH, decanoyl chloride 81%

On the other hand, the synthesis of enantiomerically pure (1S,2S)-1-phenyl-2-decanoylamino-3-morpholino-1-propanol (L-threo-PDMP) from L-serine has also been described by Mitchell, Scott A., J. Org. Chem., 63 (24), 8837-8842, 1998.

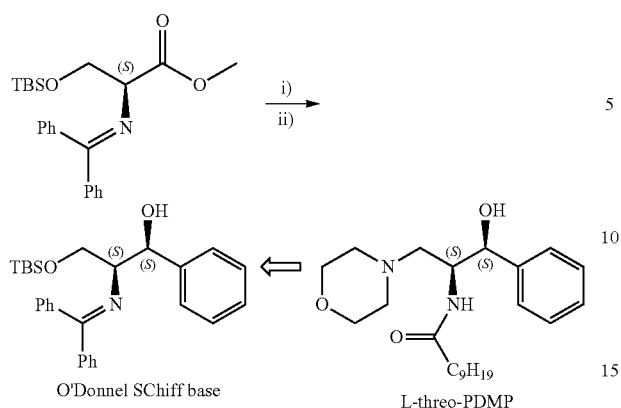

O'Donnel SChiff base

L-threo-PDMP i) iBu$_5$Al$_2$H ii) PhMgBr

Other known methods to obtain L-threo-PDMP are described by Miura, T. et al, *Bioorg. Med. Chem.*, 6, 1481-1498, 1998 and in JP-A-9-216858.

Synthesis of (1S,2S)-threo- and (1R,2S)-erythro-1-phenyl-2-palmitoylamino-3-N-morpholino-1-propanol (PPMP) were described starting from Garner aldehyde of L-serine, by Nishida, A., *Synlett*, 4, 389-390, 1998.

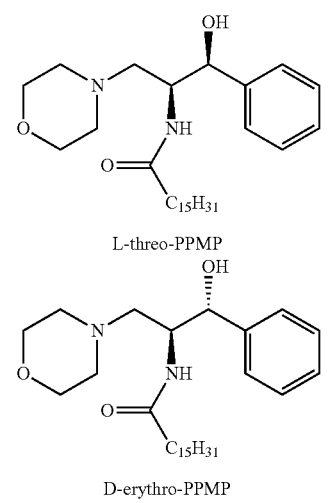

L-threo-PPMP

D-erythro-PPMP

D-threo-1-phenyl-2-palmitoylamino-3-pyrrolidino-1-propanol (P4 or PPPP) analogues were first obtained by a Mannich reaction as described Abe, A. et al., *J. Biochem.*, 111, 191-196, 1992 or U.S. Pat. No. 5,916,911 and WO 2001004108.

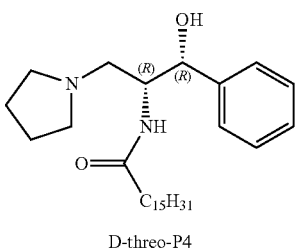

D-threo-P4

Preparation of D-threo-4'-hydroxy-P4, was described by Lee, L. et al., *J. Biol. Chem.*, 274, 21, 14662-14669, 1999. In addition, a series of dioxane substitutions was designed and tested. These included 3',4'-methylenedioxyphenyl-3',4'-ethylenedioxyphenyl-, and 3',4'-trimethylenedioxyphenyl-substituted homologues.

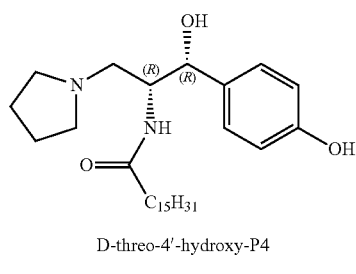

D-threo-4'-hydroxy-P4

Synthesis of enantiomerically pure D-threo-1-phenyl-2-benzyloxycarbonylamino-3-pyrrolidino-1-propanol (PBPP) and D-threo-P4 and its analogues from N-benzyloxycarbonyl-D-serine, was described by Jimbo M. et al, *J. Biochem.*, 127(3), 485-91, 2000 and EP 782992 (Seikagaku Kogyo Co.).

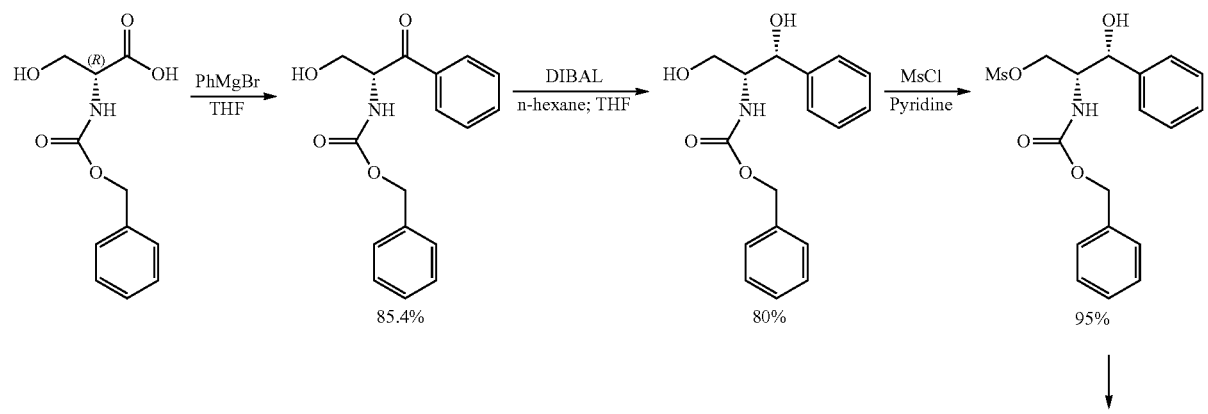

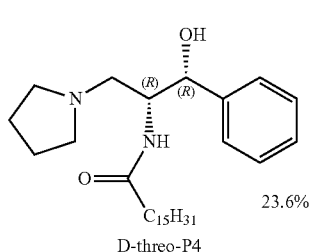 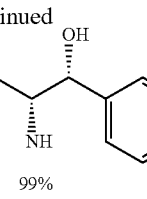 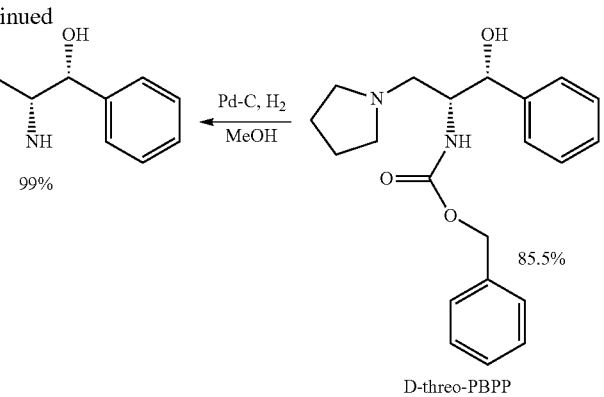

Novel prodrugs of P4 derivatives were described in US 20020198240 and WO 2002062777.

Synthesis of enantiomerically pure of D-threo-ethylenedioxy-P4 and D-threo-p-methoxy-P4 were described by Husain A. and Ganem B., *Tetrahedron Lett.*, 43, 8621-8623, 2002. The key step is a highly syn-selective additions of aryl Grignard reagents to Garner aldehyde.

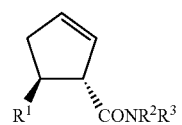

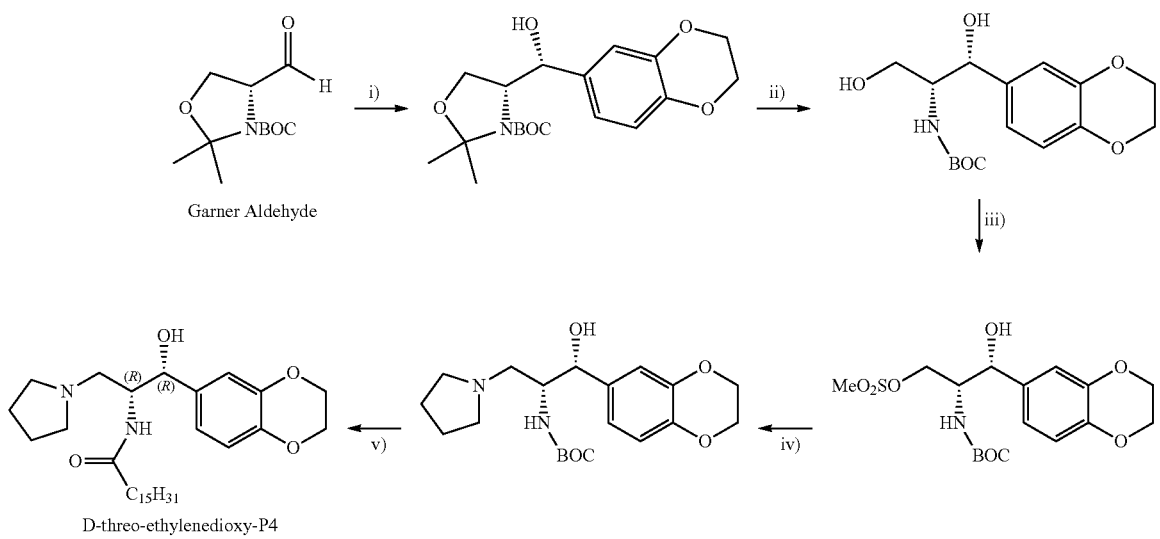

i) 3,4-ethylenedioxyphenylmagnesium bromide, -78° C., CuI, THF:Me$_2$S, 64% ii) 0.1 N HCl, THF 82%, MsCl, Et$_3$N, DCM, 0° C., 85% iii) pyrrolidine, DMF, 45° C., 58% iv) 3 N HCl, 0° C., to RT then C$_{15}$H$_{31}$COCl, Et$_3$N, DMAP, DCM, -20° C., 87%

Diastereoselective synthesis of P4 analogues were described in U.S. Ser. No. 03/015,3768 and WO 2003045928 (Genzyme Corp.); Oxazolines I [R$^1$=(un)substituted aryl; R$^2$, R$^3$=H, (un)substituted aliphatic; NR$^2$R$^3$=heterocyclic] are prepared as intermediates for P4 glucosyltransferase inhibitors from R$^1$CHO and R$^2$R$^3$NCOCH$_2$CN. Thus, methyl isocyanoacetate CNCH$_2$CO$_2$Me was treated with pyrrolidine and the amide was treated with 1,4-benzodioxane-6-carboxaldehyde, followed by hydrolysis of the oxazoline using HCl in methanol, reduction of the keto group of amide II using LiAlH$_4$, and acylation with palmitoyl chloride to give D,L-threo-ethylenedioxy-P4 III.

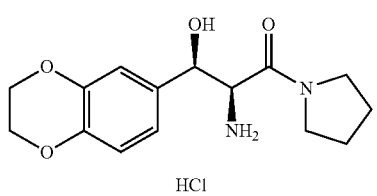

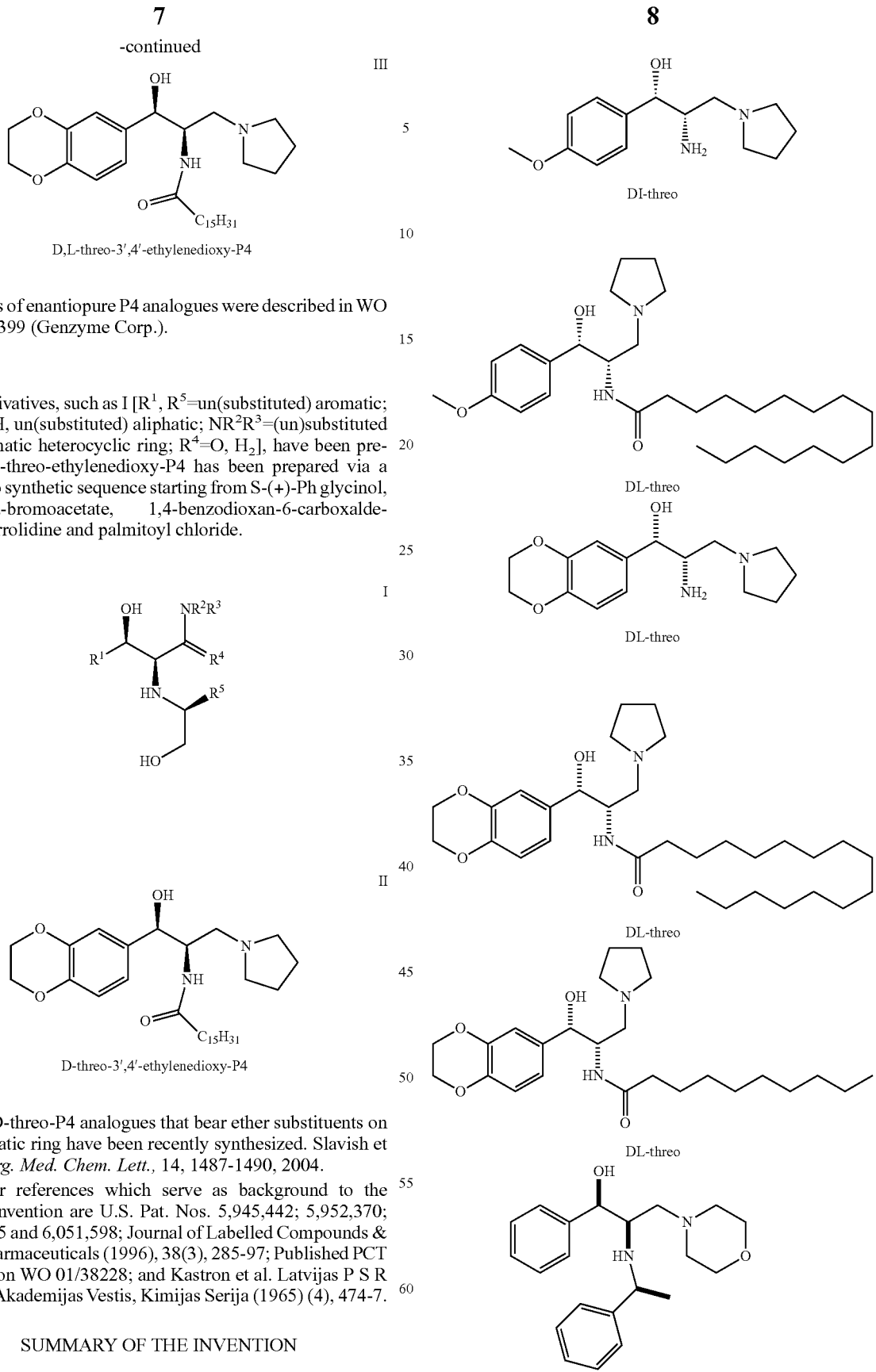

Synthesis of enantiopure P4 analogues were described in WO 2003008399 (Genzyme Corp.).

P4 derivatives, such as I [$R^1$, $R^5$=un(substituted) aromatic; $R^2$, $R^3$=H, un(substituted) aliphatic; $NR^2R^3$=(un)substituted non-aromatic heterocyclic ring; $R^4$=O, $H_2$], have been prepared. D-threo-ethylenedioxy-P4 has been prepared via a multistep synthetic sequence starting from S-(+)-Ph glycinol, phenyl-α-bromoacetate, 1,4-benzodioxan-6-carboxaldehyde, pyrrolidine and palmitoyl chloride.

New D-threo-P4 analogues that bear ether substituents on the aromatic ring have been recently synthesized. Slavish et al., *Bioorg. Med. Chem. Lett.*, 14, 1487-1490, 2004.

Further references which serve as background to the present invention are U.S. Pat. Nos. 5,945,442; 5,952,370; 6,030,995 and 6,051,598; Journal of Labelled Compounds & Radiopharmaceuticals (1996), 38(3), 285-97; Published PCT application WO 01/38228; and Kastron et al. Latvijas P S R Zinatnu Akademijas Vestis, Kimijas Serija (1965) (4), 474-7.

SUMMARY OF THE INVENTION

The present invention is directed to methods of treating a patient suffering from one or more types of cognitive disorders using the compounds set forth below:

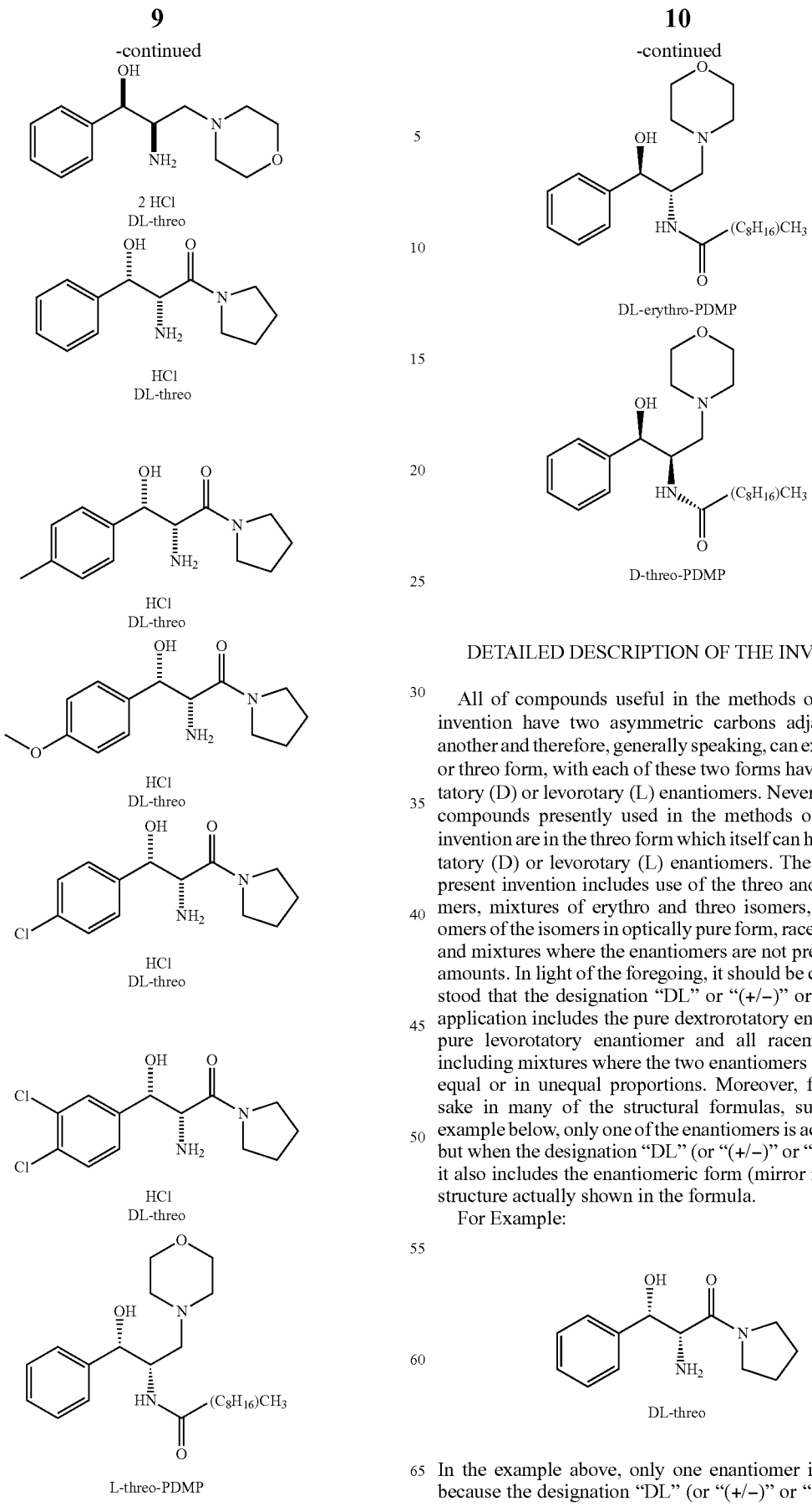

DETAILED DESCRIPTION OF THE INVENTION

All of compounds useful in the methods of the present invention have two asymmetric carbons adjacent to one another and therefore, generally speaking, can exist in erythro or threo form, with each of these two forms having dextrorotatory (D) or levorotary (L) enantiomers. Nevertheless, most compounds presently used in the methods of the present invention are in the threo form which itself can have dextrorotatory (D) or levorotary (L) enantiomers. The scope of the present invention includes use of the threo and erythro isomers, mixtures of erythro and threo isomers, both enantiomers of the isomers in optically pure form, racemic mixtures and mixtures where the enantiomers are not present in equal amounts. In light of the foregoing, it should be clearly understood that the designation "DL" or "(+/−)" or "(±)" in this application includes the pure dextrorotatory enantiomer, the pure levorotatory enantiomer and all racemic mixtures, including mixtures where the two enantiomers are present in equal or in unequal proportions. Moreover, for simplicity sake in many of the structural formulas, such as in the example below, only one of the enantiomers is actually shown but when the designation "DL" (or "(+/−)" or "(±)") appears it also includes the enantiomeric form (mirror image) of the structure actually shown in the formula.

For Example:

In the example above, only one enantiomer is shown, but because the designation "DL" (or "(+/−)" or "(±)") appears below the formula, its optical isomer

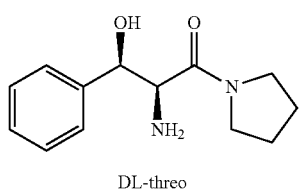 [SMILES: N[C@H](C(=O)N1CCCC1)[C@H](O)c1ccccc1]

DL-threo and all racemic mixtures of the two optical isomers are also included.

Keeping the foregoing example in mind a person of ordinary skill in the art should readily understand the scope of each described example, although in a broad sense all enantiomers and racemic mixtures are within the scope of the invention.

Generally speaking the compounds used in the methods of the present invention may already be shown as hydrochloride salts. However, the compounds may also exist in salt free form or may form salts with pharmaceutically acceptable acids, other than hydrochloric acid, and such pharmaceutically acceptable salts are also within the scope of the invention.

Any of the compounds described here may be used to treat a patient suffering from a cognitive disorder, such as an agnosia, an amnesia, an aphasia, an apraxia, a delirium, a dementia, and a learning disorder.

Biological Activity, Modes of Administration

The compounds described here may be used to treat a patient suffering from one or more types of cognitive disorder, such as an agnosia, an amnesia, an aphasia, an apraxia, a delirium, a dementia, and a learning disorder.

To "treat," as used here, means to deal with medically. It includes, for example, administering a compound of the invention to prevent the onset of a cognitive disorder, to alleviate its severity, and to prevent its reoccurrence.

The term "cognitive disorder," as used here, means any condition characterized by a deficit in mental activities associated with thinking, learning, or memory. Examples of such disorders include agnosias, amnesias, aphasias, apraxias, deliriums, dementias, and learning disorders.

In some cases, the cause of a cognitive disorder may be unknown or uncertain. In other cases, the cognitive disorder may be associated with (that is, be caused by or occur in the presence of) other conditions characterized by damage to or loss of neurons or other structures involved in the transmission of signals between neurons. Hence, cognitive disorders may be associated with neurodegenerative diseases such as Alzheimer's disease, corticobasal degeneration, Creutzfeldt-Jacob disease, frontotemporal lobar degeneration, Huntington disease, multiple sclerosis, normal pressure hydrocephalus, organic chronic brain syndrome, Parkinson's disease, Pick disease, progressive supranuclear palsy, or senile dementia (Alzheimer type); it may be associated with trauma to the brain, such as that caused by chronic subdural hematoma, concussion, intracerebral hemorrhage, or with other injury to the brain, such as that cause by infection (e.g., encephalitis, meningitis, septicemia) or drug intoxication or abuse.

Cognitive disorders may also be associated with other conditions which impair normal functioning of the central nervous system, including psychiatric disorders such as anxiety disorders, dissociative disorders, mood disorders, schizophrenia, and somatoform and factitious disorders; it may also be associated with conditions of the peripheral nervous system, such as chronic pain.

The compounds described here may be used to treat agnosias, amnesias, aphasias, apraxias, deliriums, dementias, learning disorders and other cognitive disorders regardless of whether their cause is known or not.

Examples of dementias which may be treated with the methods of the invention include AIDS dementia complex, Binswanger's disease, dementia with Lewy Bodies, frontotemporal dementia, multi-infarct dementia, Pick's disease, semantic dementia, senile dementia, and vascular dementia.

Examples of learning disorders which may be treated with the methods of the invention include Asperger's syndrome, attention deficit disorder, attention deficit hyperactivity disorder, autism, childhood disintegrative disorder, and Rett syndrome.

Examples of aphasia which may be treated with the methods of the invention include progressive non-fluent aphasia.

The compounds described here may also be used to treat patient having deficits in mental activities that are mild or that otherwise do not significantly interfere with daily life. Mild cognitive impairment is an example of such a condition: a patient with mild cognitive impairment displays symptoms of dementia (e.g., difficulties with language or memory) but the severity of these symptoms is such that a diagnosis of dementia may not be appropriate. The compounds described here may be used to treat mild cognitive impairment and other, similarly less severe forms of cognitive disorders.

Examples of Compounds of the Invention

Table 1, below, lists compounds which may be used in the method of the invention.

TABLE 1

| Compound or compound no. | Chemical Formula |
|---|---|
| L-threo-PDMP Available from Matreya, LLC | L-threo-PDMP |
| DL-erythro-PDMP Available from Matreya, LLC | DL-erythro-PDMP |

TABLE 1-continued

| Compound or compound no. | Chemical Formula |
|---|---|
| D-threo-PDMP Available from Matreya, LLC | (structure of D-threo-PDMP: phenyl-CH(OH)-CH(NHC(O)(C8H16)CH3)-CH2-morpholine) D-threo-PDMP |
| 2 | (structure: phenyl-CH(OH)-CH(NH2)-CH2-morpholine) 2·HCl L-threo |
| 1:1 Racemic mixture of 2 and 4 | (structure: phenyl-CH(OH)-CH(NH2)-CH2-morpholine) 2·HCl L-threo |
| | (structure: phenyl-CH(OH)-CH(NH2)-CH2-morpholine) 2·HCl D-threo |
| 5 | (structure: phenyl-CH(OH)-CH(NH-CH(CH3)phenyl)-CH2-morpholine) 2·HCl D-threo |

TABLE 1-continued

| Compound or compound no. | Chemical Formula |
|---|---|
| 6 | (structure: benzodioxin-CH(OH)-CH(NH2)-CH2-pyrrolidine) DL-threo |
| 7 | (structure: benzodioxin-CH(OH)-CH(NHC(O)-long alkyl chain)-CH2-pyrrolidine) DL-threo |
| 9 | (structure: 4-methoxyphenyl-CH(OH)-CH(NH2)-CH2-pyrrolidine) DL-threo |
| 15 | (structure: 3,4-dichlorophenyl-CH(OH)-CH(NH2)-C(O)-pyrrolidine) HCl DL-threo |
| 16 | (structure: phenyl-CH(OH)-CH(NH2)-C(O)-pyrrolidine) HCl DL-threo |
| 17 | (structure: 4-methylphenyl-CH(OH)-CH(NH2)-C(O)-pyrrolidine) HCl DL-threo |

Modes of Administration:

Compounds useful in the methods of the invention are administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. For human adults such doses generally will be in the range of 0.1-5,000 mg/day; more preferably in the range of 1 to 3,000 mg/day, 10 mg to 500 mg/day, 500 to 1,000 mg/day, 1,000 to 1,500 mg/day, 1,500 to 2,000 mg/day, 2,000 to 2,500 mg/day, or 2,500 to 3,000 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

Preferably, the patient will be given the compound in a composition orally in any pharmaceutically acceptable form, such as a tablet, liquid, capsule, powder and the like. However, other routes may be desirable or necessary, particularly if the patient suffers from nausea. Such other routes may include, without exception, transdermal, intraperitonial, parenteral, subcutaneous, intranasal, intrathecal, intramuscular, intravenous and intrarectal modes of delivery and the present invention extends to pharmaceutical compositions adapted for such deliveries. Pharmaceutical compositions tend to contain a pharmaceutically acceptable excipient. Such excipient are well known in the art and may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations of the compositions may also include wetting agents, emulsifying agents, preserving agents, sweetening agents, and/or flavoring agents. If used as in an ophthalmic or infusion format, the formulation will usually contain one or more salt to influence the osmotic pressure of the formulation.

Methods for Obtaining Compounds Useful for the Method of the Invention

Compounds useful in the methods of the invention are known in the art and can be obtained from commercial sources or by the synthetic processes described in the pertinent references (primarily in Shin, S. et al., [*Tetrahedron asymmetry*, 11, 3293-3301, 2000] and US 20030153768) and noted in the Background Art section of the present application. For the purposes of the present invention the majority of the compounds were nevertheless synthesized and their preparations are described below.

General $^1$H NMR spectra were recorded at ambient temperature with an Avance 300 (Bruker) spectrometer. The compounds were analyzed by reverse phase high performance liquid chromatography (HPLC) using a Waters Autopurification System equipped with a Waters 2525 Pump, a Waters 2696 photodiode array detector, and a XTerra column (Part. No. 186000482, 5 μm, C18, 4.5×50 mm).

The HPLC method used was a gradient of 5% solvent B to 100% in 7 min. Solvent A was $H_2O$ with 0.05% TFA and solvent B was $CH_3CN$ with 0.05% TFA (Method A). Melting points were measured with a Büchi B-545 melting point apparatus and were uncorrected. To isolate reaction products the solvent were removed by evaporation using a vacuum rotatory evaporator, the water bath temperature not exceeding 40° C.

Preparation of Compound 6, Compound 7, Compound 8 and Compound 9

2-Isocyano-1-(pyrrolidin-1-yl)ethanone BLE 04098

To stirred and cooled (0° C.) methyl isocyanoacetate (96% technical grade, 5.0 g, 47.8 mmol) was slowly added in 0.75 h pyrrolidine (6.5 mL, 78 mmol). The mixture was stirred for 1.5 h with continued cooling and then concentrated. The resulting oil was co-evaporated twice from $CH_2Cl_2$:hexane to remove residual pyrrolidine. 2-Isocyano-1-(pyrrolidin-1-yl)ethanone BLE 04098 was obtained as a yellow solid (6.85 g, 98% yield) and used in the next step without purification.

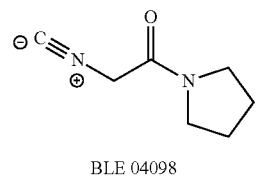

BLE 04098

MW: 138.17; Yield: 98%; yellow solid; Mp (° C.)=73.9.
$^1$H-NMR (CDCl$_3$, δ): 1.81-2.08 (m, 4H, 2×CH$_2$), 3.35-3.45 (m, 2H, —NCH$_2$), 3.50-3.60 (m, 2H, —NCH$_2$), 4.23 (s, 2H, CH$_2$CO).

trans-(4,5-Dihydro-5-(2,3-dihydrobenzo[b][1,4]dioxin-6-yl)oxazol-4-yl)(pyrrolidin-1-yl)methanone BLE 04100

To a stirred and cooled (0° C.) solution of potassium hydroxide (0.43 mg, 7.60 mmol) in MeOH (6.5 mL) were added successively 1,4-benzodioxan-6-carboxaldehyde (1.31 g, 7.96 mmol) and 2-isocyano-1-(pyrrolidin-1-yl)ethanone BLE 04098 (1.0 g, 6.57 mmol). The solution was stirred 3 h at 0° C. and then concentrated. The residue was partitioned between EtOAc (100 mL) and water. The organic layer was combined with 2 additional EtOAc extracts (2×100 mL), washed with brine, dried over MgSO$_4$, filtered and evaporated. Concentration afford to a crude product which was purified by column chromatography on silica (EtOAc) to yield, after evaporation and drying, to trans-4,5-dihydro-5-(2,3-dihydrobenzo[b][1,4]dioxin-6-yl)oxazol-4-yl)(pyrrolidin-1-yl)methanone BLE 04100 as a colourless oil (1.76 g, 89% yield).

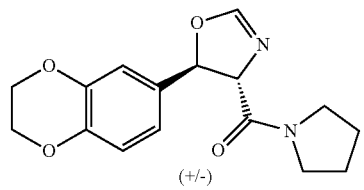

BLE 04100

MW: 440.49; Yield: 89%; colourless oil.
$^1$H-NMR (CDCl$_3$, δ): 1.75-2.10 (m, 4H, 2×CH$_2$), 3.40-3.59 (m, 6H, 3×CH$_2$N), 3.85-4.00 (m, 1H, CHN), 4.26 (s, 4H, CH$_2$O), 4.59 (dd, 1H, J=7.5 Hz, J=2.2 Hz, CH—N), 6.00 (d, 1H, J=7.5 Hz, CH—O), 6.75-6.90 (m, 3H, ArH), 7.00 (d, 1H, J=2.2 Hz, CH=N).

trans-(4,5-Dihydro-5-(4-methoxyphenyl)oxazol-4-yl)(pyrrolidin-1-yl)methanone SLA 07074

To a stirred and cooled (0° C.) solution of potassium hydroxide (0.37 g, 6.57 mmol) in methanol (30 mL) was added a mixture of 4-methoxy-benzaldehyde (0.88 mL, 7.23 mmol) and 2-isocyano-1-(pyrrolidin-1-yl)ethanone BLE 04098 (1.0 g, 6.57 mmol). The solution was stirred 4 h with continued cooling and then concentrated. The residue was partitioned between ethyl acetate and water. The organic layer was combined with additional ethyl acetate extracts, washed with aqueous sodium chloride and dried over MgSO$_4$. Concentration afforded a crude product as a glassy solid. Flash chromatography over silica (ethyl acetate) yielded to trans-(4,5-dihydro-5-(4-methoxyphenyl)oxazol-4-yl)(pyrrolidin-1-yl)methanone SLA 07074 as a pale yellow solid (1.2 g, 90.5%).

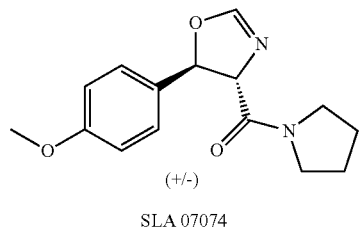 [SMILES: COc1ccc([C@H]2OC=N[C@@H]2C(=O)N2CCCC2)cc1]

SLA 07074

MW: 274.32; Yield: 90.5%; pale yellow solid; Mp (° C.): 91.2.

R$_f$: 0.30 (EtOAc).

$^1$H-NMR (CDCl$_3$, δ): 1.75-2.08 (m, 4H, 2×CH$_2$), 3.40-3.58 (m, 3H, CH$_2$N), 3.52 (s, 3H, CH$_3$O), 3.88-3.98 (m, 1H, CH$_2$N), 4.59 (dd, 1H, J=7.6 Hz, J=2.2 Hz, CH—N), 6.06 (d, 1H, J=7.6 Hz, CH—O), 6.90 (d, 2H, J=8.7 Hz, ArH), 7.01 (d, 1H, J=2.2 Hz, CH=N), 7.25 (d, 2H, J=8.7 Hz, ArH).

MS-ESI m/z (% rel. Int.): 275.1 ([MH]$^+$, 10), 247.1 (100).

HPLC: Method A, detection UV 280 nm, SLA 07074 RT=5.2 min, peak area 92%.

DL-threo-2-Amino-3-hydroxy-3-(4-methoxyphenyl)-1-(pyrrolidin-1-yl)propan-1-one hydrochloride SLA 07078

To a stirred solution of trans-(4,5-dihydro-5-(4-methoxyphenyl)oxazol-4-yl)(pyrrolidin-1-yl)methanone SLA 07074 (1.61 g, 5.93 mmol) in methanol (13 mL) was added hydrochloric acid (1 mL). After heating at 50° C. for 3 h the mixture reaction was concentrated and the resulting yellow oil was co-evaporated twice with ethyl acetate before solidifying. Trituration (ethyl acetate) and drying afforded DL-threo-2-amino-3-hydroxy-3-(4-methoxyphenyl)-1-(pyrrolidin-1-yl)propan-1-one hydrochloride SLA 07078 as a white solid (1.64 g, 93%).

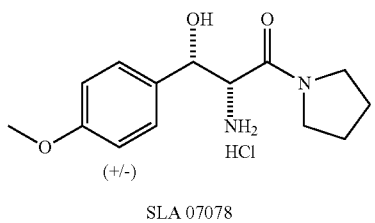 [SMILES: COc1ccc([C@H](O)[C@@H](N)C(=O)N2CCCC2)cc1 ; Cl]

SLA 07078

MW: 300.78; Yield: 93%; white Solid; Mp (° C.): 177.0.

$^1$H-NMR (CD$_3$OD, δ): 1.32-1.50 (m, 1H, CH$_2$), 1.50-1.88 (m, 3H, CH$_2$), 2.15-2.28 (m, 1H, CH$_2$N), 3.15-3.42 (m, 4H, 2×CH$_2$N), 3.79 (s, 3H, CH$_3$O), 4.06 (d, 1H, J=9.2 Hz, CH—N), 4.78 (d, 1H, J=9.2 Hz, CHO), 6.94 (d, 2H, J=8.5 Hz, ArH), 7.34 (d, 2H, J=8.5 Hz, ArH).

$^{13}$C-NMR (CD$_3$OD, δ): 24.8, 26.6, 47.2, 47.6, 55.9, 59.6, 73.9, 115.0 (2×C), 128.9 (2×C), 132.5, 161.7, 166.4.

DL-threo-2-amino-3-(2,3-dihydrobenzo[b][1,4]dioxin-6-yl)-3-hydroxy-1-(pyrrolidin-1-yl)propan-1-one hydrochloride Compound 12

To a stirred solution of trans-4,5-dihydro-5-(2,3-dihydrobenzo[b][1,4]dioxin-6-yl)oxazol-4-yl)(pyrrolidin-1-yl)methanone BLE 04100 (1.74 g, 5.77 mmol) in methanol (15 mL) was added hydrochloric acid (1 mL). After heating at 50° C. for 3 h the mixture reaction was concentrated and the resulting yellow oil was co-evaporated twice with ethyl acetate before solidifying. Trituration (ethyl acetate) and drying afforded DL-threo-2-amino-3-(2,3-dihydrobenzo[b][1,4]dioxin-6-yl)-3-hydroxy-1-(pyrrolidin-1-yl)propan-1-one hydrochloride Compound 12 as a white solid (1.85 g, 95%).

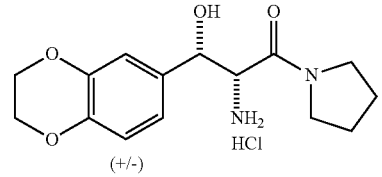

Compound 12

MW: 328.79; Yield: 95.0%; White Solid; Mp (° C.): 176.2.

$^1$H-NMR (CD$_3$OD, δ): 1.42-1.58 (m, 1H, CH$_2$), 1.58-1.70 (m, 1H, CH$_2$), 1.70-1.88 (m, 2H, CH$_2$), 3.20-3.45 (m, 4H, N—CH$_2$), 4.06 (d, 1H, J=9.1 Hz, CH—N), 4.25 (s, 2H, CH$_2$), 4.75 (d, 1H, J=9.2 Hz, CH—O), 4.89 (s, 2H, CH$_2$), 6.82-6.95 (m, 3H, ArH).

$^{13}$C-NMR (CD$_3$OD, δ): 24.9, 26.7, 47.3, 47.6, 59.5, 65.7, 73.6, 116.4, 118.3, 120.3, 133.7, 145.1, 145.6, 166.4.

DL-threo-2-Amino-1-(2,3-dihydrobenzo[b][1,4]dioxin-6-yl)-3-(pyrrolidin-1-yl)propan-1-ol Compound 6

To a stirred suspension of trans-(4,5-dihydro-5-(4-methoxyphenyl)oxazol-4-yl)(pyrrolidin-1-yl)methanone SLA 07074 (1.79 g, 5.44 mmol) in THF (220 mL) was slowly added at 0° C., in two portions, LiAlH$_4$ (1.28 g, 33.7 mmol). The mixture was stirred at RT for 3.5 h and quenched by a slow addition of water at 0° C. (350 mL). The white suspension was concentrated to remove THF and taken back in a mixture of CH$_2$Cl$_2$ (300 mL) and 1 N aqueous HCl (50 mL). The aqueous layer was basified to pH=10-11 by slow addition of 1 N aqueous NaOH. The organic layer was removed; two more extracts were combined and dried over MgSO$_4$, filtered and evaporated. Concentration afforded to a crude product as a yellow oil. This material was purified by column chromatography on silica (CH$_2$Cl$_2$:MeOH:NH$_4$OH 20%=94:5:1) to led to DL-threo-2-amino-1-(2,3-dihydrobenzo[b][1,4]dioxin-6-yl)-3-(pyrrolidin-1-yl)propan-1-ol Compound 6 (0.705 g, 46.5% yield) as a near colorless gum.

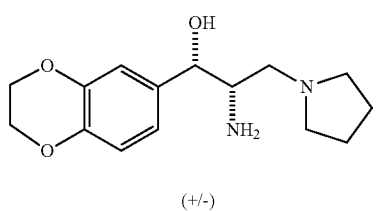

Compound 6

(+/-)

MW: 278.35; Yield: 46.5%; Colorless Gum.

$R_f$: 0.20 ($CH_2Cl_2$:MeOH:$NH_4OH$ 20%=94:5:1).

$^1$H-NMR ($CDCl_3$, δ): 1.70-1.85 (m, 4H, 2×$CH_2$), 2.40-2.70 (m, 6H, 3×$CH_2N$—), 3.05-3.15 (m, 1H, CH—N), 4.25 (s, 4H, $CH_2O$), 4.55 (d, 1H, J=2.2 Hz, CH—O), 5.30 (s, 1H, —OH), 6.75-6.90 (m, 3H, ArH).

N-(DL-threo-1-(2,3-dihydrobenzo[b][1,4]dioxin-6-yl)-1-hydroxy-3-(pyrrolidin-1-yl)propan-2-yl)decanamide Compound 7

To a stirred solution of DL-threo-2-amino-1-(2,3-dihydrobenzo[b][1,4]dioxin-6-yl)-3-(pyrrolidin-1-yl)propan-1-ol Compound 12 (0.186 g, 0.67 mmol) in 10 mL $CH_2Cl_2$ were added, in order, N-hydroxysuccinimide (0.081 g, 0.70 mmol) in 2 mL $CH_2Cl_2$, triethylamine (112 μL, 0.80 mmol) and decanoyl chloride (125 μL, 0.60 mmol). The mixture was stirred overnight at RT and then partitioned between $CH_2Cl_2$ and 1 N aqueous sodium hydroxide. The organic layer was dried over $MgSO_4$, filtered and evaporated and the residue obtained was purified by column chromatography on silica ($CH_2Cl_2$:MeOH=95:5). A white solid N-(DL-threo-1-(2,3-dihydrobenzo[b][1,4]dioxin-6-yl)-1-hydroxy-3-(pyrrolidin-1-yl)propan-2-yl)palmitamide Compound 7 was obtained (126 mg, 43.5% yield).

Compound 7

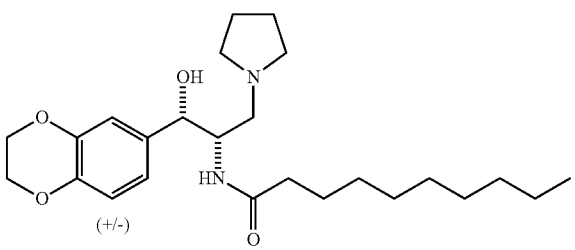

(+/-)

MW: 516.76; Yield: 43.5%; White Solid; Mp (° C.): 84.6.

$R_f$: 0.40 (MeOH:$CH_2Cl_2$=10:90).

$^1$H-NMR ($CDCl_3$, δ): 0.88 (t, 3H, J=6.7 Hz, $CH_3$), 1.12-1.39 (m, 12H), 1.40-1.60 (m, 2H, $CH_2$), 1.72-1.90 (m, 4H, 2×$CH_2$), 2.10 (t, 2H, J=6.7 Hz, $CH_2$), 2.55-2.90 (m, 6H), 4.13-4.30 (m, 1H, CH—N), 4.24 (s, 4H, $CH_2N$), 4.91 (d, 1H, J=3.3 Hz, CH—O), 5.90 (d, 1H, J=7.4 Hz, NH), 6.75-6.88 (m, 3H, ArH), OH not seen.

$^{13}$C-NMR ($CDCl_3$, δ): 14.1, 22.7, 23.6 (2×C), 25.6, 29.1, 29.3, 31.9, 36.8, 52.3, 55.1 (2×C), 57.7, 64.3 (2×C), 75.2, 77.2, 115.0, 117.0, 118.9, 134.4, 142.8, 143.4, 173.5, 174.8.

MS-ESI m/z (% rel. Int.): 433.1 ([MH]$^+$, 100).

HPLC: Method A, detection UV 280 nm, Compound 7, RT=5.2 min, peak area 96.2%.

N-(DL-threo-1-(2,3-Dihydrobenzo[b][1,4]dioxin-6-yl)-1-hydroxy-3-(pyrrolidin-1-yl)propan-2-yl)palmitamide Compound 8

To a stirred solution of DL-threo-2-amino-1-(2,3-dihydrobenzo[b][1,4]dioxin-6-yl)-3-(pyrrolidin-1-yl)propan-1-ol Compound 12 (0.158 g, 0.57 mmol) in 10 mL $CH_2Cl_2$ were added, in order, N-hydroxysuccinimide (0.068 g, 0.59 mmol) in 2 ml $CH_2Cl_2$, triethylamine (95 μL, 0.68 mmol) and palmitoyl chloride (155 μL, 0.511 mmol) in 3 mL $CH_2Cl_2$. The mixture was stirred overnight at RT and then partitioned between $CH_2Cl_2$ and 1 N aqueous sodium hydroxyde. The organic layer was purified by column chromatography on silica using as eluent $CH_2Cl_2$:MeOH=95:5. A white solid N-(DL-threo-1-(2,3-dihydrobenzo[b][1,4]dioxin-6-yl)-1-hydroxy-3-(pyrrolidin-1-yl)propan-2-yl)palmitamide Compound 8 was obtained (148 mg, 50.4% yield).

Compound 8

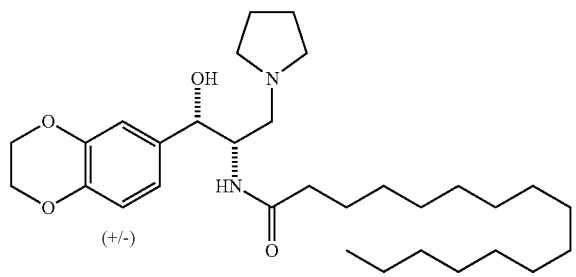

(+/-)

MW: 516.7; Yield: 50.4%; White Solid; Mp (° C.): 66.4.

$R_f$: 0.50 (MeOH:$CH_2Cl_2$=10:90).

$^1$H-NMR ($CDCl_3$, δ): 0.88 (t, 3H, J=6.7 Hz, $CH_3$), 1.15-1.35 (m, 24H), 1.45-1.58 (m, 2H, $CH_2$), 1.75-1.90 (m, 4H, 2×$CH_2$), 2.10 (t, 2H, J=7.4 Hz, $CH_2$), 2.61 (s, 1H, OH), 2.52-2.72 (m, 4H), 2.72-2.92 (m, 2H), 4.15-4.22 (m, 1H, CH—N), 4.24 (s, 4H, $CH_2N$), 4.92 (d, 1H, J=3.3 Hz, CH—O), 6.08 (d, 1H, J=7.4 Hz, NH), 6.75-6.90 (m, 3H, ArH).

MS-ESI m/z (% rel. Int.): 517.2 ([MH]$^+$, 100).

HPLC: Method A, detection UV 280 nm, Compound 8 RT=6.60 min, peak area 97.2%.

DL-threo-2-Amino-1-(4-methoxyphenyl)-3-(pyrrolidin-1-yl)propan-1-ol Compound 9

To a stirred suspension of DL-threo-[5-(4-methoxy-phenyl)-4,5-dihydro-oxazol-4-yl]-pyrrolidin-1-yl-methanone SLA 07078 (1.61 g, 5.35 mmol) in tetrahydrofuran (200 mL) under nitrogen atmosphere was slowly added, in two portions, lithium aluminium hydride (1.22 g, 32.12 mmol) at 0° C. The mixture reaction was stirred at RT for 17 h, and then quenched by a slow, dropwise addition of water (50 mL). The white suspension was then concentrated to remove THF and taken back up in a mixture of 300 mL $CH_2Cl_2$ and 1 N aqueous hydrochloric acid (50 mL). The aqueous layer was basified to pH=10-11 by a slow addition of 1N aqueous sodium hydroxyde. The organic layer was removed, combined with additional $CH_2Cl_2$ extracts (4×200 mL) and dried over $MgSO_4$, filtered and evaporated. The crude product was purified by column chromatography on silica ($CH_2Cl_2$:MeOH:$NH_3$=94:05:01). After evaporation and drying, DL-threo-2-amino-1-(4-methoxyphenyl)-3-(pyrrolidin-1-yl)propan-1-ol Compound 9 was obtained (0.62 g, 46%) as a pale yellow solid.

Compound 9

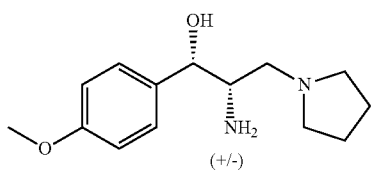

(+/-)

MW: 250.34; Yield: 46%; Pale Yellow Solid; Mp (° C.): 77.7.

$R_f$: 0.35 ($CH_2Cl_2$:MeOH:$NH_3$=94:05:01).

$^1$H-NMR ($CDCl_3$, δ): 1.65-1.87 (s, 4H, 2×$CH_2$), 2.40-2.90 (m, 9H, $CH_2N$, $NH_2$ & OH), 3.11-3.17 (m, 1H, CH—N), 3.81 (s, 3H, $CH_3O$), 4.61 (d, 1H, J=3.8 Hz, CH—O), 7.89 (d, 2H, J=8.6 Hz, ArH), 7.26 (d, 2H, J=8.5 Hz, ArH).

$^{13}$C-NMR ($CDCl_3$, δ): 23.6 (2×C), 54.5, 54.7 (2×C), 55.3, 60.1, 75.9, 113.6, 127.4, 134.4, 158.8.

MS-ESI m/z (% rel. Int.): 251.1 ([MH]$^+$, 100).

Preparation of Compound 2, 4 and 5

Benzyl (S)-3-hydroxy-1-oxo-1-phenylpropan-2-ylcarbamate TTA 08010B

To a stirred solution of Z-L-Ser-OH (6.00 g, 25.08 mmol) in 32 mL of anhydrous THF at 0° C. under nitrogen was added dropwise 1 M phenylmagnesium bromide in THF (32 mL, 200 mmol). The mixture was stirred 15 h at RT under nitrogen. A solution of 2 M HCl (100 mL) was slowly added at 0° C. and the mixture was partitioned between ethyl acetate (750 mL) and acidic water. The organic layer was washed with water (2×20 mL), 1 N aqueous sodium bicarbonate (2×20 mL), brine (2×20 mL) and dried over $MgSO_4$. After removing ethyl acetate by evaporation at 30-35° C., the crude product (4.50 g, 60% yield) was cristallized in a mixture of ethyl acetate:hexane=25 mL:20 mL to give benzyl (S)-3-hydroxy-1-oxo-1-phenylpropan-2-ylcarbamate TTA 08010B as a white solid (1.40 g, 20% yield).

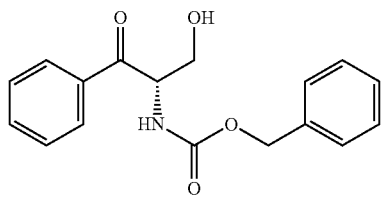

TTA 08010B

MW: 299.32; Yield: 20%; White Solid; Mp (° C.): 106.5. $R_f$: 0.75 ($CH_2Cl_2$:MeOH=9:1).

$^1$H-NMR ($CDCl_3$, δ): 2.78 (s, 1H, OH), 3.85-3.93 (m, 1H, $CH_2O$), 4.00-4.09 (m, 1H, $CH_2O$), 5.14 (s, 2H, $ArCH_2O$), 5.40 (t, 1H, J=3.3 Hz, CH), 6.17 (d, 1H, J=6.4 Hz, NH), 7.35 (s, 5H, ArH), 7.49 (t, 2H, J=7.60 Hz, ArH), 7.62 (t, 1H, J=7.1 Hz, ArH), 8.99 (t, 2H, J=7.6 Hz, ArH).

$^{13}$C-NMR ($CDCl_3$, δ): 58.3, 64.6, 67.3, 128.1, 128.3, 128.6, 128.7, 129.0, 134.1, 136.0, 156.6, 196.6.

MS-ESI m/z (% rel. Int.): 300.1 ([MH]$^+$, 5), 256.1 (100).

HPLC: Method A, detection UV 254 nm, TTA 08010B RT=5.40 min, peak area 98.5%.

$[α]^{22}_D$=−5.8 (c=1.00, MeOH).

Benzyl L-threo-1,3-dihydroxy-1-phenylpropan-2-ylcarbamate TTA 08012

To a stirred solution of benzyl (S)-3-hydroxy-1-oxo-1-phenylpropan-2-ylcarbamate TTA 08010B (1.40 g, 4.70 mmol) in 28 mL of anhydrous THF at −78° C. under nitrogen was added slowly dropwise 1 M DIBAL-H in hexane (18.8 mL, 18.80 mmol). The mixture was stirred 2 h at −78° C. then 1.5 h at RT. A solution of 2 M HCl (35 mL) was slowly added at −20° C. and the mixture was partitioned between ethyl acetate (750 mL) and acidic water. The organic phase was washed with water (2×20 mL), brine (2×20 mL) and dried over $MgSO_4$. After removing ethyl acetate by evaporation at 30-35° C., the crude product was purified by column chromatography on silica ($CH_2Cl_2$:MeOH=98:2 to 97:3) to give benzyl L-threo-1,3-dihydroxy-1-phenylpropan-2-ylcarbamate TTA 08012 as a white solid (1.10 g, 78% yield).

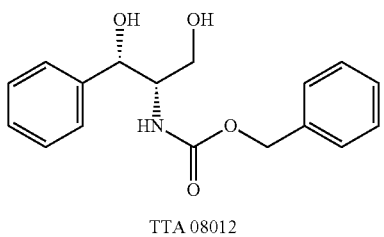 [SMILES: O=C(N[C@@H](CO)[C@@H](O)c1ccccc1)OCc1ccccc1]

TTA 08012

MW: 301.34; Yield: 78%; White Solid; Mp (° C.): 102.5. $R_f$: 0.30 ($CH_2Cl_2$:MeOH=95/5).

$^1$H-NMR ($CDCl_3$, δ): 3.08 (t, 1H, J=5.0 Hz, OH), 3.59 (d, 1H, J=3.1 Hz, OH), 3.64-3.78 (m, 2H, $CH_2O$), 3.80-3.89 (m, 1H, CH), 4.95 (s, 2H, $ArCH_2O$), 5.57 (d, 1H, J=8.3 Hz, NH), 7.17-7.38 (m, 10H, ArH).

$^{13}$C-NMR ($CDCl_3$, δ): 57.5, 63.6, 66.9, 73.8, 126.0, 127.8, 127.9, 128.1, 128.5, 128.6, 136.2, 141.0, 156.9.

MS-ESI m/z (% rel. Int.): 302.0 ([MH]$^+$, 5); 132.0 (100).

HPLC: Method A, detection UV 254 nm, TTA 08012 RT=5.00 min, peak area 99.5%.

$[α]^{22}_D$=+39.4 (c=1.00, MeOH).

Benzyl L-threo-1-hydroxy-3-morpholino-1-phenylpropan-2-ylcarbamate hydrochloride Compound 1

To a stirred solution of benzyl L-threo-1,3-dihydroxy-1-phenylpropan-2-ylcarbamate TTA 08012 (1.00 g, 3.30 mmol) in 13 mL of pyridine at −10° C. was added dropwise methanesulfonyl chloride (0.27 mL, 3.50 mmol). The mixture was stirred 6 h at 20° C. under nitrogen. Pyridine was removed by evaporation at 30-35° C. and the residue was partitioned between ethyl acetate (250 mL) and 0.1 N HCl (20 mL). The organic phase was washed with water (20 mL), brine (20 mL), dried over $MgSO_4$ and evaporated to give after drying L-threo-1-hydroxy-3-methanesulfonyl-1-phenylpropan-2-ylcarbamate TTA 08014 (1.25 g, 65% yield).

To a stirred solution of crude benzyl L-threo-1-hydroxy-3-methanesulfonyl-1-phenylpropan-2-ylcarbamate TTA 08014 (1.25 g, 3.30 mmol) in 6 mL of DMF at RT was added morpholine (1.2 mL, 13.20 mmol). The mixture was stirred 15 h at 50° C. under nitrogen. DMF was evaporated and the residue was partitioned between ethyl acetate (250 mL) and 1 N aqueous sodium bicarbonate (20 mL). The organic phase was washed with water (20 mL), brine (20 mL) and dried over MgSO$_4$. After evaporation the crude product was purified by column chromatography on silica (CH$_2$Cl$_2$:MeOH=98:2 to 97:3) to give benzyl L-threo-1-hydroxy-3-morpholino-1-phenylpropan-2-ylcarbamate as an oil (380 mg, 31% yield). The hydrochloride salt was obtained from 100 mg of the free base in diethylether at 0° C. using a solution 0.3 M HCl in diethylether. The precipitate was filtered and dry to give benzyl L-threo-1-hydroxy-3-morpholino-1-phenylpropan-2-ylcarbamate hydrochloride Compound 1 as a white solid (70 mg, 65% yield).

Compound 1

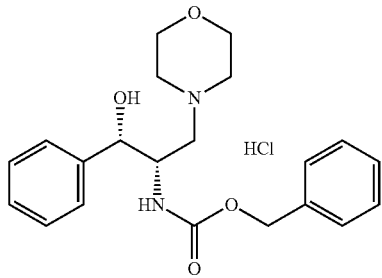

MW: 406.90; Yield: 20%; White Solid; Mp (° C.): 144.5.
R$_f$: 0.40 (CH$_2$Cl$_2$:MeOH=95:5).
$^1$H-NMR (CD$_3$OD, δ): 3.14-3.77 (m, 6H, CH$_2$N), 3.70-4.07 (m, 4H, CH$_2$O), 4.30-4.33 (m, 1H, CH), 4.90-5.06 (m, 3H, CH, ArCH$_2$O), 7.20-7.43 (m, 10H, ArH).
$^{13}$C-NMR (CD$_3$OD, δ): 51.2, 51.8, 53.2, 59.3, 63.2, 66.3, 72.5, 125.8, 127.2, 127.3, 127.5, 127.8, 127.9.
MS-ESI m/z (% rel. Int.): 371.0 ([MH]$^+$, 100).
HPLC: Method A, detection UV 254 nm, Compound 1 RT=4.40 min, peak area 96.5%.
[α]$^{22}_D$=+13.9 (c=1.00, MeOH).

L-threo-2-Amino-3-morpholino-1-phenylpropan-1-ol dihydrochloride Compound 2

To a stirred solution of benzyl L-threo-1-hydroxy-3-morpholino-1-phenylpropan-2-ylcarbamate Compound 1 (0.26 g, 0.70 mmol) in 20 mL of MeOH at RT was added Pd—C 10% (140 mg). The mixture was saturated with hydrogen and stirred for 24 h at RT under hydrogen atmosphere (balloon). The catalyst Pd—C 10% was removed by filtration on celite and the solution was evaporated. The crude product was purified by column chromatography on silica (CH$_2$Cl$_2$:MeOH:NH$_4$OH=79:20:1 to 75:20:5) to give L-threo-2-amino-3-morpholino-1-phenylpropan-1-ol as an oil (100 mg, 60% yield). The hydrochloride salt was obtained from 83 mg of the free base in diethylether at 0° C. using 0.3 M HCl in diethylether. After precipitation in diethylether, filtration and drying L-threo-2-amino-3-morpholino-1-phenylpropan-1-ol dihydrochloride Compound 2 was obtained as a white solid (80 mg, 74% yield).

Compound 2

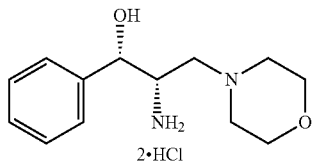

MW: 309.23; Yield: 44.0%; White Solid; Mp (° C.): 166.4-170.9.
R$_f$: 0.20 (CH$_2$Cl$_2$:MeOH=9:1).
$^1$H-NMR (CD$_3$OD, δ): 3.30-3.77 (m, 6H, CH$_2$N), 3.92-4.05 (m, 4H, CH$_2$O), 4.05-4.16 (m, 1H, CH), 4.85-4.98 (m, 1H, CH), 7.35-7.60 (m, 5H, ArH).
$^{13}$C-NMR (CD$_3$OD, δ): 53.1, 54.9, 58.5, 64.8, 72.6, 127.2, 128.0, 130.2, 140.3.
MS-ESI m/z (% rel. Int.): 237.0 ([MH]$^+$, 100).
HPLC: Method A, detection UV 254 nm, Compound 2 RT=0.90 min, peak area 98.0%.
[α]$^{22}_D$=+10.8 (c=1.00, MeOH), free base: [α]$^{22}_D$=−6.1 (c=0.25, CHCl$_3$).

Preparation of D-threo-2-amino-3-morpholino-1-phenylpropan-1-ol dihydrochloride Compound 4

(R)-Methyl 1-((S)-1-phenylethyl)aziridine-2-carboxylate EBE 06044B

To solution of methyl 2,3-dibromopropionate (25 mL, 198 mmol) in toluene at 5° C. was added triethylamine (55 mL, 0.39 mmol) in toluene (100 mL). After stirring for 5 min (S)-(1)-phenethylamine (25 mL, 198 mmol) in toluene (100 mL) was added dropwise. The suspension was refluxed for 3 h and allowed to cool down, filtered and the volatiles were evaporated under reduced pressure to give a residue that was purified by column chromatography (950 g of silica gel) with a gradient of 0-20% EtOAc in cyclohexane to yield to (S)-methyl 1-((S)-1-phenylethyl)aziridine-2-carboxylate EBE 06044A as a yellow oil (17.31 g, 43% yield) and (R)-methyl 1-((S)-1-phenylethyl)aziridine-2-carboxylate EBE 06044B as a yellow oil (15.14 g, 37% yield).

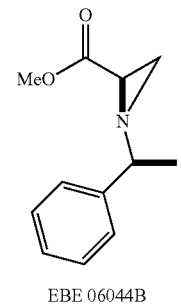

EBE 06044B

MW: 205.3; Yield EBE 06044B: 37%; Yellow Oil. Yield: EBE 06044A: 43%, Yellow Oil.
R$_f$: EBE 06044A=0.5; R$_f$: EBE 06044B=0.35 (EtOAc:cyclohexane=25:75).
$^1$H-NMR (CDCl$_3$, δ): EBE 06044A: 1.47 (d, 3H, J=6.6 Hz, CH$_3$), 1.60 (d, 1H, J=6.4 Hz, CH), 2.13 (d, 1H, J=2.6 Hz), 2.21 (dd, 1H, J=3.2 Hz, J=6.4 Hz), 2.54 (q, 1H, J=6.6 Hz), 3.75 (s, 3H, OCH$_3$) 7.23-7.40 (m, 5H, ArH).
$^1$H-NMR (CDCl$_3$, δ): EBE 06044B: 1.46 (d, 3H, J=6.6 Hz, CH$_3$), 1.79 (d, 1H, J=6.6 Hz, CH), 2.08 (d, 1H, J=3.11 Hz, 6.6 Hz), 2.34 (dd, 1H, J=3.1 Hz, J=1.0 Hz), 2.56 (q, 1H, J=6.6 Hz), 3.67 (s, 3H, OCH$_3$) 7.24-7.36 (m, 5H, ArH).
$^{13}$C-NMR (CDCl$_3$, δ): EBE 06044B: 23.5, 35.0, 36.9, 52.2, 69.8, 126.5, 127.2, 128.5, 143.6, 171.1.
HPLC: Method A, detection at 254 nm, EBE 06044B RT=6.11 min, peak area 92.9%.

((R)-1-((S)-1-Phenylethyl)aziridin-2-yl)methanol EBE 06046

A 250 mL round bottom flask was charged with anhydrous THF (100 mL) and LiAlH$_4$ (2.77 g, 73.1 mmol). While the suspension is stirred at 0° C., a solution of (S)-methyl 1-((S)-1-phenylethyl)aziridine-2-carboxylate EBE 06044B (10.0 g, 48.7 mmol) in THF (50 mL) was added dropwise over 20 min. The dropping funnel was washed with THF (2×3 mL) and allowed to react 20 min at 0° C. Maintaining the reaction mixture at 0° C., a solution of KOH (10%, 20 mL) was added dropwise for 20 min (caution the reaction is exothermic). The mixture was stirred for 0.5 h at 25° C. and the white precipitate removed by filtration through a celite pad that was washed with diethyl ether (30 mL). The combined organic filtrates were washed with NaH$_2$PO$_4$ and the aqueous layer was extracted with Et$_2$O (3×30 mL). The combined organic phase were dried with Na$_2$SO$_4$ and concentrated to give ((R)-1-((S)-1-phenylethyl)aziridin-2-yl)methanol EBE 06046 as a white solid (10.4 g, 90% yield).

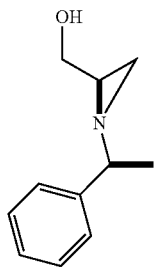

EBE 06046

MW: 177.2; Yield: 90%; White Solid; Mp (° C.): 37.7.

$^1$H-NMR (CDCl$_3$, δ): 1.43 (d, 3H, J=6.6 Hz, CH$_3$), 1.49 (d, 1H, J=6.5 Hz, CH), 1.65-1.71 (m, 1H, CH), 1.92 (d, 1H, J=3.5 Hz, NCH), 2.26 (s, 1H, OH), 2.53 (q, 1H, J=6.6 Hz, NCH), 3.32-3.37 (m, 1H, OCH$_2$), 3.56 (m, 1H, OCH$_2$), 7.23-7.35 (m, 5H, ArH).

$^{13}$C-NMR (CDCl$_3$, δ): 22.9, 31.4, 39.3, 62.5, 69.4, 126.6, 127.3, 128.6, 144.5.

(R)-1-((S)-1-Phenylethyl)aziridine-2-carbaldehyde EBE 06048

A three neck, 250 mL round bottom flask was equipped with a low temperature thermometer and two (2) equalizing dropping funnels. One of these was connected to a nitrogen line and charged with a solution of ((R)-1-((S)-1-phenylethyl)aziridin-2-yl)methanol EBE 06046 (7.0 g, 39.5 mmol) in CH$_2$Cl$_2$ (75 mL), the other was charged with a solution of DMSO (9.25 g, 118.5 mmol) in CH$_2$Cl$_2$ (11 mL). To a solution of oxalyl chloride (7.5 g, 59.3 mmol) in CH$_2$Cl$_2$ (90 mL) under N$_2$ at −78° C., the DMSO solution was added dropwise during 20 min and stirred for 20 min. EBE 06046 (7.0 g, 39.5 mmol) in CH$_2$Cl$_2$ (75 mL) was added dropwise over 50 min. then the dropping funnel was charged with DIEA (42.6 mL, 237 mmol) in CH$_2$Cl$_2$ (10 mL) and the reaction mixture was stirred for 30 min at −45° C. The DIEA solution was added over 5 min with the reaction mixture at −78° C. and the reaction was allowed to warm to room temperature. The reaction mixture was washed with H$_2$O (3×50 mL), dried over MgSO$_4$, filtered, evaporated. The crude product obtained was purified by column chromatography on silica with a gradient of 0-20% [v/v] EtOAc in cyclohexane to give (R)-1-((S)-1-phenylethyl)aziridine-2-carbaldehyde EBE 06048 as a yellow oil (5.59 g, 81% yield).

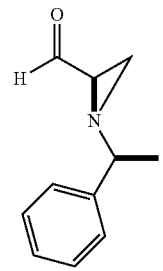

EBE 06048

MW: 175.2; Yield: 81%; Yellow Oil.

R$_f$: EBE 06048: 0.3 (EtOAc:cyclohexane=20:80).

$^1$H-NMR (CDCl$_3$, δ): 1.47 (d, 3H, J=6.6 Hz, CH$_3$), 1.94 (d, 1H, J=6.7 Hz, NCH$_2$), 2.08 (dt, J=2.9 Hz, J=6.4 Hz, NCH), 2.37 (d, 1H, J=2.6 Hz, NCH$_2$), 2.61 (q, 1H, J=6.6 Hz, NCH), 7.20-7.38 (m, 5H, ArH), 8.92 (d, 1H, J=6.2 Hz).

$^{13}$C-NMR (CDCl$_3$, δ): 22.7, 32.1, 43.2, 68.1, 125.5, 126.5, 127.6, 142.4, 198.7.

(R)-Phenyl((R)-1-((S)-1-phenylethyl)aziridin-2-yl)methanol EBE 06066

To a solution of bromobenzene (4.93 g, 31.4 mmol) in THF 125 mL under nitrogen at −78° was added t-BuLi (1.7 M in pentane, 50 mL). The mixture was stirred for 0.5 h at room temperature. The mixture was cooled down to −78° C. and a solution of (R)-1-((S)-1-phenylethyl)aziridine-2-carbaldehyde EBE 06048 (2.5 g, 14.3 mmol) in THF (16.7 mL) at −78° C. was added dropwise. The reaction mixture was treated with H$_2$O (20 mL), the organic layer was separated and the aqueous phase was extracted with EtOAc. The combined organic layers were dried over MgSO$_4$, filtered and concentrated in vacuo to give a residue that was purified by column chromatography using a gradient of 0-20% [v/v] EtOAc in cyclohexane to give (R)-phenyl((R)-1-((S)-1-phenylethyl)aziridin-2-yl)methanol EBE 06066 (3.13 g, 86% yield).

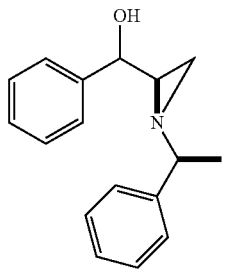

EBE 06066

MW: 253.3; Yield 86%.

R$_f$: =0.3 (EtOAc:cyclohexane=20:80).

$^1$H-NMR (CDCl$_3$, δ): 1.47 (d, 3H, J=6.6 Hz, CH$_3$), 1.57 (d, 1H, J=6.5 Hz, CH), 1.79 (dt, 1H, J=3.5 Hz, J=8.7 Hz, CH), 2.04 (d, 1H, J=3.5 Hz, OCH), 2.35 (bs, 1H, OH), 2.53 (q, 1H, J=6.5 Hz, CH), 4.23 (d, 1H, J=5.7 Hz, OCH), 7.07-7.13 (m, 2H, ArH), 7.16-7.20 (m, 3H, ArH), 7.24-7.34 (m, 5H, ArH).

$^{13}$C-NMR (CDCl$_3$, δ): 22.4, 32.0, 44.6, 69.4, 74.1, 125.8 (2×C), 126.9 (2×C), 127.3, 127.6, 128.2 (2×C), 128.7 (2×C), 142.0, 144.2.

[α]$^{22}_D$=−71.53 (c=0.59, CHCl$_3$).

D-threo-2-((S)-1-Phenylethylamino)-3-morpholino-1-phenylpropan-1-ol dihydrochloride Compound 5

To a solution of (R)-phenyl((R)-1-((S)-1-phenylethyl)aziridin-2-yl)methanol EBE 06066 (1.5 g, 5.92 mmol) in CH₃CN (19 mL) at RT was added iodotrimethylsilane (3.55 g, 17.8 mmol). The solution was stirred for 2 h and morpholine (1.032 g, 11.84 mmol) was added. After 2 h at reflux, the reaction mixture was treated with HCl (1 M) to reach pH=1 and stirred for 10 min. After a slow addition of NaHCO₃ to reach pH=9, the product was extracted with EtOAc, dried over Na₂SO₄, filtered to give after evaporation a crude brown oil that was purified by column chromatography using a gradient of 0-20% [v/v] MeOH in EtOAc to give D-threo-2-((S)-1-phenylethylamino)-3-morpholino-1-phenylpropan-1-ol EBE 06068A (0.831 g, 42%) as a pale brown solid. To a solution of D-threo-2-((S)-1-phenylethylamino)-3-morpholino-1-phenylpropan-1-ol EBE 06068A (0.100 g, 0.294 mmol) in ethanol (1 mL) was added a solution of HCl (0.8 M, 0.816 mL) in EtOH. Evaporation of the volatiles afforded to D-threo-2-((S)-1-phenylethylamino)-3-morpholino-1-phenylpropan-1-ol dihydrochloride Compound 5 as white solid (0.125 g, 100%).

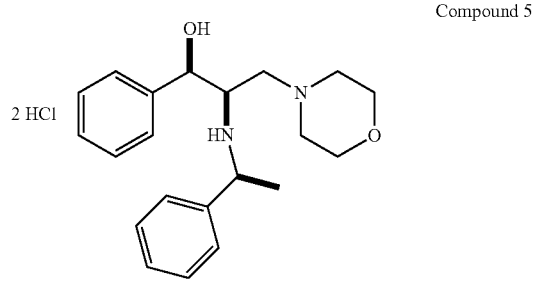 [SMILES: C[C@H](N[C@H](CN1CCOCC1)[C@H](O)c1ccccc1)c1ccccc1]

Compound 5

MW: 412.37; Yield: 42%; White Solid; Mp (° C.): 157.2 (dec).

$R_f$: 0.3 (MeOH:EtOAc=20:80) EBE 06068A.

¹H-NMR (CD₃OD, δ): 1.19 (t, 2H, J=7.0 Hz, NCH₂), 1.71 (d, 3H, J=6.8 Hz, CH₃), 3.45 (m, 2H, J=7.1 Hz, NCH₂), 3.62 (q, 2H, J=7.1 Hz, N—CH₂), 3.97 (t, 4H, J=4.5 Hz, OCH₂), 4.06 (m, 1H, CH—N), 4.75 (q, 1H, J=6.8 Hz, CH—N), 5.21 (d, 1H, J=5.1 Hz, CH—O), 7.44-7.56 (m, 10H, ArH).

MS-ESI m/z (% rel. Int.): 341.1 ([MH]⁺, 20).

¹³C-NMR (CD₃OD, δ): 24.4, 54.5 (2×C), 55.5, 55.9, 60.0, 67.0 (2×C), 75.6, 126.3 (2×C), 126.5 (2×C), 127.0, 127.1, 128.1 (2×C), 128.5 (2×C), 142.2, 145.3.

HPLC: Method A, detection at 254 nm, Compound 5 RT=4.41 min, peak area 99%.

D-threo-2-Amino-3-morpholino-1-phenylpropan-1-ol dihydrochloride Compound 4

To a solution of D-threo-2-((S)-1-phenylethylamino)-3-morpholino-1-phenylpropan-1-ol EBE 06068A (0.400 g, 1.17 mmol) in MeOH (6 mL) at RT was added acetic acid (0.133 mL, 2.35 mmol). The reaction vessel was flushed with nitrogen and Pd(OH)₂ (25% weight, 0.150 g) was added. The nitrogen atmosphere was exchanged with hydrogen using three cycle of vacuum and hydrogen addition using a balloon of hydrogen. After stirring for 16 hours under hydrogen the reaction mixture was filtrated through celite to give EBE 06070A the acetate salt of (2R)-amino-3-morpholin-4-yl-(1R)-phenyl-propan-1-ol (0.279 g, 98% yield). To as solution of EBE 06070A the acetate salt of (2R)-amino-3-morpholin-4-yl-(1R)-phenyl-propan-1-ol (0.100 g, 0.338 mmol) in ethanol (1 mL) was added a solution of HCl (0.8 M, 0.930 mL) in EtOH. Evaporation of the volatiles afforded to D-threo-2-amino-3-morpholino-1-phenylpropan-1-ol dihydrochloride Compound 4 (0.104 g, 100% yield) as an off white solid. (Adapted from Shin, S.-H.; Han, E. Y.; Park, C. S.; Lee, W. K.; Ha, H.-J. *Tetrahedron Asymmetry*, 2000, 11, 3293-3301).

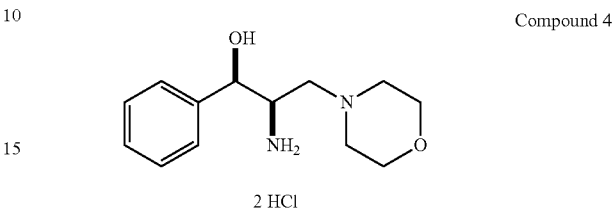

Compound 4

MW: 309.23; Yield: 99%; Off White Solid; Mp (° C.): 183.4.

¹H-NMR (CD₃OD, δ): 3.30-3.77 (m, 6H, CH₂N), 3.92-4.05 (m, 4H, CH₂O), 4.05-4.16 (m, 1H, CH), 4.85-4.98 (m, 1H, CH), 7.35-7.60 (m, 5H, ArH).

¹³C-NMR (CD₃OD, δ): 53.2, 58.3, 58.5 (2×C), 64.9 (2×C), 72.6, 128.0 (2×C), 130.2 (2×C), 140.3.

MS-ESI m/z (% rel. int.): 237.1 (100, [MH]⁺).

HPLC: Isocratic 10% CH₃CN in H₂O (pH 10, [NH₄OH]=5 mM), detection UV 254 nm, Compound 4 RT=6.63 min, peak area 97.3%.

$[\alpha]^{22}_D = -10.7$ (c=1.00, MeOH).

Preparation of Compound 13, Compound 14, Compound 15, Compound 16 and Compound 17

Method B:

To a stirred and cooled (0° C.) solution of potassium hydroxide (380 mg, 5.80 mmol) in MeOH (5 mL) were added successively aldehyde (5.80 mmol) and 2-isocyano-1-(pyrrolidin-1-yl)ethanone BLE 04098 (0.8 g, 5.8 mmol). The solution was stirred 3 h at 0° C. and then concentrated. The residue was partitioned between CH₂Cl₂ (100 mL) and water. The organic layer was washed with brine, dried over MgSO₄, filtered and evaporated. Concentration afford to a crude product which was purified by column chromatography on silica (cyclohexane:EtOAc=70/30 to 0:100) to yield, after evaporation and drying, to an intermediate oxazoline. To a stirred solution of oxazoline in methanol (15 mL) was added hydrochloric acid (1 mL, 12 mmol). After heating at 60° C. for 2 h, the mixture reaction was then concentrated and the resulting yellow oil was coevaporated twice with MeOH before solidifying. Trituration in EtOAc:MeOH=10/1 followed by filtration gave title compound as a white solid.

DL-threo-2-Amino-3-hydroxy-3-(4-methoxyphenyl)-1-(pyrrolidin-1-yl)propan-1-one hydrochloride Compound 13

The compound was prepared according to method B with 4-methoxybenzaldehyde (811 mg, 5.80 mmol). DL-threo-2-Amino-3-hydroxy-3-(4-methoxyphenyl)-1-(pyrrolidin-1-yl)propan-1-one hydrochloride Compound 13 was obtained as a white solid (468 mg, 30% yield).

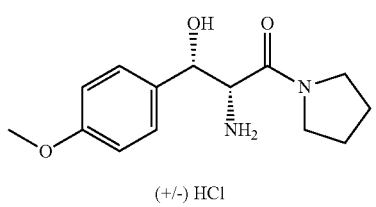

Compound 13

(+/-) HCl

MW: 300.78; Yield: 30.0%; White Solid; Mp (° C.):176.6.
R$_f$: 0.15 (EtOAc:MeOH=85:15) free base.
$^1$H-NMR (CD$_3$OD, δ): 1.37-1.78 (m, 4H, 2×CH$_2$), 2.17-2.25 (m, 1H, CH$_2$N), 3.15-3.26 (m, 2H, CH$_2$N), 3.34-3.40 (m, 2H, CH$_2$N), 3.79 (s, 3H, CH$_{3O}$), 4.06 (d, 1H, J=9.3 Hz, CH—N), 4.80 (d, 1H, J=9.3 Hz, CH—O), 6.94 (m, 2H, J=8.7 Hz, ArH), 7.33 (d, 2H, J=8.6 Hz, ArH).
$^{13}$C-NMR (CD$_3$OD, δ): 24.8, 26.6, 47.2, 47.6, 55.9, 59.6, 73.8, 115.0, 128.9, 132.5, 161.7, 166.4.
MS-ESI m/z (% rel. Int.): 265.1 ([MH]$^+$, 10), 247.1 (100).
HPLC: Method A, detection UV 254 nm, Compound 13 RT=3.70 min, peak area 99.00%.

DL-threo-2-Amino-3-(4-chlorophenyl)-3-hydroxy-1-(pyrrolidin-1-yl)propan-1-one hydrochloride Compound 14

The compound was prepared according to method B with 4-chlorobenzaldehyde (837 mg, 5.80 mmol). DL-threo-2-Amino-3-(4-chlorophenyl)-3-hydroxy-1-(pyrrolidin-1-yl)propan-1-one hydrochloride Compound 14 was obtained as a white solid (483 mg, 33% yield).

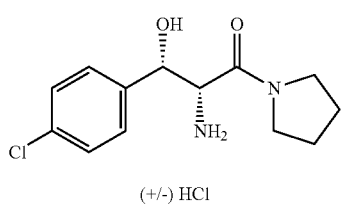

Compound 14

(+/-) HCl

MW: 321.24; Yield: 33.0%; White Solid; Mp (° C.): 190.1.
R$_f$: 0.15 (EtOAc:MeOH=85:15), free base.
$^1$H-NMR (CD$_3$OD, δ): 1.41-1.78 (m, 4H, 2×CH$_2$), 2.24-2.32 (m, 1H, CH$_2$N), 3.16-3.28 (m, 2H, CH$_2$N), 3.34-3.40 (m, 1H, CH$_2$N), 4.11 (d, 1H, J=9.0 Hz, CH—N), 4.85-4.88 (m, 1H, CH—O), 7.42 (s, 4H, ArH).
$^{13}$C-NMR (CD$_3$OD, δ): 24.8, 26.6, 47.2, 47.6, 59.2, 73.5, 129.4, 129.8, 135.8, 139.6, 166.1.
MS-ESI m/z (% rel. Int.): 269.1/271.1 ([MH]$^+$, 50/20), 251.1/253.1 (100/30).
HPLC: Method A, detection UV 254 nm, Compound 14 RT=4.00 min, peak area 99.00%.

DL-threo-2-Amino-3-(3,4-dichlorophenyl)-3-hydroxy-1-(pyrrolidin-1-yl)propan-1-one hydrochloride Compound 15

The compound was prepared according to method B with 3,4-dichlorobenzaldehyde (809 mg, 4.60 mmol). DL-threo-2-Amino-3-(3,4-dichlorophenyl)-3-hydroxy-1-(pyrrolidin-1-yl)propan-1-one hydrochloride Compound 15 was obtained as a white solid (522 mg, 31% yield).

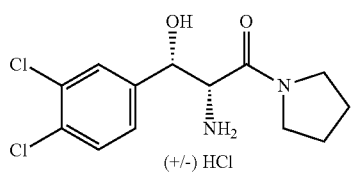

Compound 15

(+/-) HCl

MW: 355.69; Yield: 31.0%; White Solid; Mp (° C.): 186.3.
R$_f$: 0.15 (EtOAc:MeOH=85:15), free base.
$^1$H-NMR (CD$_3$OD, δ): 1.46-1.82 (m, 4H, 2×CH$_2$), 2.32-2.40 (m, 1H, CH$_2$N), 3.20-3.27 (m, 1H, CH$_2$N), 3.34-3.43 (m, 2H, CH$_2$N), 4.15 (d, 1H, J=8.7 Hz, CH—N), 4.87-4.90 (m, 1H, CH—O), 7.38 (dd, 1H, J=8.3 Hz, J=1.7 Hz, ArH), 7.57-7.59 (m, 2H, ArH).
$^{13}$C-NMR (CD$_3$OD, δ): 24.9, 26.7, 47.3, 47.8, 59.0, 72.8, 127.5, 129.8, 131.9, 133.6, 133.7, 141.6, 166.0.
MS-ESI m/z (% rel. Int.): 303.1/305.0 ([MH]$^+$, 65/45), 111.0 (100).
HPLC: Method A, detection UV 254 nm, Compound 15 RT=4.20 min, peak area 99.00%.

DL-threo-2-Amino-3-hydroxy-3-phenyl-1-(pyrrolidin-1-yl)propan-1-one hydrochloride Compound 16

The compound was prepared according to method B with benzaldehyde (0.613 g, 5.78 mmol). DL-threo-2-Amino-3-hydroxy-3-phenyl-1-(pyrrolidin-1-yl)propan-1-one hydrochloride Compound 16 was obtained as a white solid (0.225 g, 14% yield).

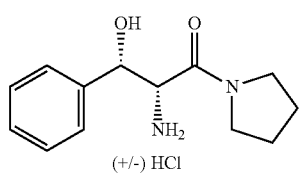

Compound 16

(+/-) HCl

MW: 270.76; Yield: 14%; White Solid; Mp (° C.): 184.9.
$^1$H-NMR (CD$_3$OD, δ): 1.30-1.42 (m, 1H, CH$_2$), 1.50-1.60 (m, 1H, CH$_2$), 1.60-1.80 (m, 2H, CH$_2$), 2.05-2.15 (m, 1H, CH$_2$), 3.12-3.30 (m, 2H, NCH$_2$), 3.30-3.40 (m, 1H, NCH$_2$), 4.09 (d, 1H, J=9.2 Hz, CH—N), 4.80-4.95 (m, 1H, CH—O), 7.30-7.45 (m, 5H, ArH).
$^{13}$C-NMR (CD$_3$OD, δ): 24.7, 26.5, 47.2, 47.5, 59.5, 74.2, 127.7, 129.7, 130.0, 140.8, 166.3.
MS-ESI m/z (% rel. Int.): 235.2 ([MH]$^+$, 100).
HPLC: Method A, detection UV 254 nm, Compound 16 RT=3.56 min, peak area 96.4%.

DL-threo-2-Amino-3-hydroxy-1-(pyrrolidin-1-yl)-3-p-tolylpropan-1-one hydrochloride Compound 17

The compound was prepared according to method B with 4-methyl-benzaldehyde (0.694 g, 5.78 mmol). DL-threo-2-Amino-3-hydroxy-1-(pyrrolidin-1-yl)-3-p-tolylpropan-1-one hydrochloride Compound 17 was obtained as a white solid (0.044 g, 3% yield).

Compound 17

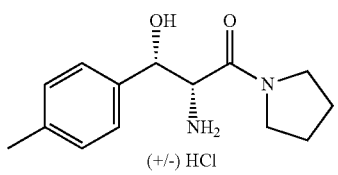

(+/−) HCl

MW: 284.78; Yield: 3%; White Solid; Mp (° C.): 184.2.

$^1$H-NMR (CD$_3$OD, δ): 1.28-1.40 (m, 1H, CH$_2$), 1.50-1.60 (m, 1H, CH$_2$), 1.60-1.80 (m, 2H, CH$_2$), 2.10-2.22 (m, 1H, CH$_2$), 2.34 (s, 3H, CH$_3$), 3.10-3.25 (m, 2H, NCH$_2$), 3.25-3.40 (m, 1H, NCH$_2$), 4.07 (d, 1H, J=9.2 Hz, CH—N), 4.80 (d, 1H, J=9.2 Hz, CH—O), 7.21 (d, 2H, J=8.1 Hz, ArH), 7.30 (d, 2H, J=8.0 Hz, ArH)

$^{13}$C-NMR (CD$_3$OD, δ): 21.2, 24.8, 26.5, 47.2, 47.5, 59.6, 74.1, 127.6, 130.2, 137.7, 140.1, 166.4.

MS-ESI m/z (% rel. Int.): 249.2 ([MH]$^+$, 30).

HPLC: Method A, detection UV 254 nm, Compound 17 RT=3.90 min, peak area 99.9%.

1-Phenyl-2-decanoylamino-3-morpholino-1-propanol (PDMP) isomers and enantiomers

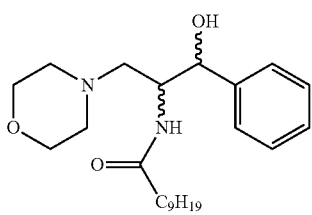

PDMP
mixture of DL-erythro and
DL-threo isomers

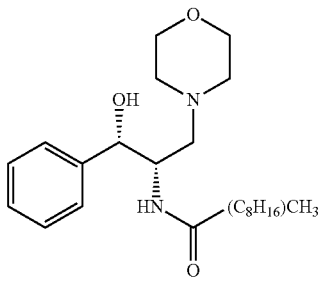

L-threo-PDMP

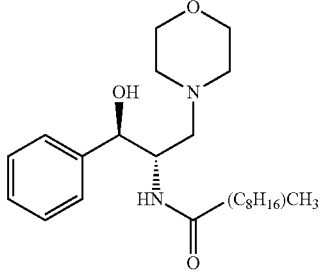

DL-erythro-PDMP

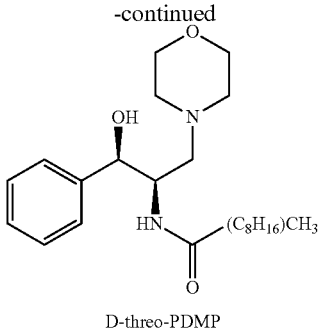

D-threo-PDMP

The above shown isomers and enantiomers, as applicable, of 1-phenyl-2-decanoylamino-3-morpholino-1-propanol (PDMP) are available commercially from Matreya, LLC, and can be prepared in accordance with the applicable references described in the background art section of the present application. Specifically, preparation of PDMP is described in Inokuchi, J. et al., *J. Lipid Res.* 28, 565-571, 1987; Radin, A. et al., *NeuroProtocols,* 3(2), 145-55, 1993; Radin, A. et al., *J. Lipid Res.* 36, 611-621, 1995 and U.S. Pat. No. 5,916,911 which are incorporated herein by reference. Enantiomerically pure D-threo-PDMP has been reported by Mitchell, Scott A. [*J. Org. Chem.,* 63 (24), 8837-8842, 1998]; Miura, T. et al, [Bioorg. Med. Chem., 6, 1481-1498, 1998]; Shin, S. et al., [*Tetrahedron asymmetry,* 11, 3293-3301, 2000]; WO 2002012185 which are incorporated herein by reference. Synthesis of enantiomerically pure L-threo-PDMP is described by Mitchell, Scott A., [*J. Org. Chem.,* 63 (24), 8837-8842, 1998]; Miura, T. et al, [*Bioorg. Med. Chem.,* 6, 1481-1498, 1998]; and JP-A-9-216858, which are incorporated herein by reference.

What is claimed is:
1. A method of preparing a compound of

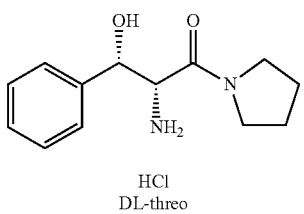 [SMILES: N[C@@H](C(=O)N1CCCC1)[C@@H](O)c1ccccc1]

HCl
DL-threo or any pharmaceutically acceptable salt thereof, the method of preparing comprising: reacting a mixture comprising potassium hydroxide, methanol, and

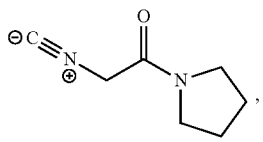

and benzaldehyde.

* * * * *